US011697654B2

(12) United States Patent
Rajasekaran et al.

(10) Patent No.: US 11,697,654 B2
(45) Date of Patent: Jul. 11, 2023

(54) KINASE INHIBITORS EXHIBITING ANTI-CANCER ACTIVITY AND THEIR METHOD OF USE

(71) Applicant: ALLCRON PHARMA INC., Glen Mills, PA (US)

(72) Inventors: Ayyappan Rajasekaran, Glen Mills, PA (US); Jon Swanson, Weldon Spring, MO (US); Peter Kane, Devon (GB); Julia Foster, Devon (GB)

(73) Assignee: ALLCRON PHARMA INC., Glen Mills, PA (US)

( * ) Notice: Subject to any disclaimer, the term of this patent is extended or adjusted under 35 U.S.C. 154(b) by 201 days.

(21) Appl. No.: 16/979,602

(22) PCT Filed: Mar. 18, 2019

(86) PCT No.: PCT/US2019/022686
§ 371 (c)(1),
(2) Date: Sep. 10, 2020

(87) PCT Pub. No.: WO2019/182944
PCT Pub. Date: Sep. 26, 2019

(65) Prior Publication Data

US 2021/0040104 A1 Feb. 11, 2021

Related U.S. Application Data

(60) Provisional application No. 62/647,098, filed on Mar. 23, 2018.

(51) Int. Cl.
*C07D 491/056* (2006.01)
*A61K 31/4741* (2006.01)
*A61P 35/00* (2006.01)

(52) U.S. Cl.
CPC .......... *C07D 491/056* (2013.01); *A61P 35/00* (2018.01)

(58) Field of Classification Search
CPC .. C07D 491/056; A61K 31/4741; A61P 35/00
See application file for complete search history.

(56) References Cited

U.S. PATENT DOCUMENTS

2009/0163545 A1* 6/2009 Goldfarb ................ A61K 31/13 514/688
2015/0140071 A1* 5/2015 Rajasekaran .......... A61K 47/20 424/93.73

FOREIGN PATENT DOCUMENTS

WO 2014/207213 12/2014

OTHER PUBLICATIONS

International Search Report and Written Opinion in PCT/US2019/022686 dated Jun. 20, 2019.
International Preliminary Report on Patentability in PCT/US2019/022686 dated Sep. 29, 2020.

* cited by examiner

*Primary Examiner* — Bruck Kifle
(74) *Attorney, Agent, or Firm* — Licata & Tyrrell P.C.

(57) ABSTRACT

Pharmaceutical compositions of the invention comprise kinase inhibitors having a disease-modifying action in the treatment of diseases associated with BCR-ABL activity that include cancer, including chronic myeloid leukemia, acute lymphoblastic leukemia, acute myeloid leukemia, chronic lymphocytic leukemia, multiple myeloma, lymphomas, and metastatic carcinoma.

7 Claims, 6 Drawing Sheets

Compound AP-R357
K562-T315I

Compound AP-R357
R357
BV-173 T315I

Compound AP-
Ba/F3-T315I

AP-R352

KINASE INHIBITORS EXHIBITING ANTI-CANCER ACTIVITY AND THEIR METHOD OF USE

CROSS-REFERENCE TO RELATED APPLICATIONS

This application is the National Stage of International Application No. PCT/US2019/022686, filed Mar. 18, 2019, and claims the benefit of priority of U.S. Provisional Application No. 62/647,098 filed Mar. 23, 2018, the teachings of each of which are herein incorporated by reference in their entirety.

FIELD OF INVENTION

The present invention describes compounds and methods useful as kinase inhibitors, useful for the treatment of cancer and related conditions. The present invention further describes compositions of said kinase inhibitors useful for the treatment of cancer.

BACKGROUND OF THE INVENTION

Chronic Myeloid Leukemia (CML) is one of the most common blood cancers in adults. American Cancer Society estimates that in 2019, 8990 new cases of CML will be diagnosed and 1140 people will die of this disease in the United States of America (https://www.cancer.org/cancer/chronic-myeloid-leukemia/about/statistics.htm). In CML, the white blood cell count in the blood increases dramatically. The disease has three phases: 1) chronic phase, 2) accelerated phase, and 3) blast crisis. Patients in the chronic phase can live for 10 to 25 years with proper medications. In the accelerated phase the survival is 3-6 years and in blast crisis survival is only 6 to 9 months.

CML is characterized by the presence of an oncogene called BCR-ABL in the leukemic cells. This oncogene is generated by the reciprocal translocation of segments of chromosomes 9 and 22 resulting in the formation of Philadelphia chromosome (Ph). A subset of acute lymphoblastic leukemia (ALL) in children and adults also contains Ph and is designated as Ph positive (Ph+) ALL. BCR-ABL oncogene codes for a tyrosine kinase the activity of which increases the proliferative potential of CML and Ph+ ALL cells. BCR-ABL protein is present in all three phases of CML disease. However, in the accelerated phase and blast crisis in addition to BCR-ABL there are many other genetic abnormalities in the CML cells.

The kinase inhibitor called Imatinib also known as Gleevec blocks the activity of BCR-ABL kinase and stops the progression of CML. Imatinib specifically targets BCR-ABL in leukemia cells by binding to its kinase domain. Patients in the chronic phase of the disease respond well to Imatinib. However, patients in the accelerated phase and blast crisis do not respond consistently to this drug. This is due to mutations in the BCR-ABL that prevents Imatinib binding to the kinase domain.

There are about 32,000 patients who are resistant to Imatinib in the United States. Many of these patients respond to second and third generation drugs (e.g. Dasatinib and Ponatinib/Iclusig™). A group of patients with BCR-ABL mutation T315I (threonine to isoleucine at the 315th amino acid) poorly respond to any of the currently available drugs. In the United States, there are about 6500 patients with BCR-ABL T315I mutation. These patients are treated with a third generation drug called Iclusig™, also called Ponatinib. While this drug binds to the BCR-ABL T315I mutant and inhibits its action, it has severe cardiovascular and neurological side effects. The FDA approved this drug in 2012 but retracted the approval in 2013 due to its toxicity. It was reapproved for clinical use since there were no other alternative drugs for CML patients with BCR-ABL T315I mutation. Thus there is an urgent need for a new drug that will stop the action of BCR-ABL T315I mutant.

BRIEF SUMMARY OF THE INVENTION

The present invention is directed toward novel compounds of formula (I), (I)

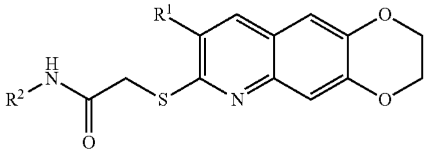

including enantiomers, diastereomers, tautomers, hydrates, solvates, pharmaceutically acceptable salts, prodrugs, and complexes thereof, wherein:

$R^1$ is selected from the group consisting of $C_{1-6}$ alkyl and nitrile;

$R^2$ is selected from the group consisting of

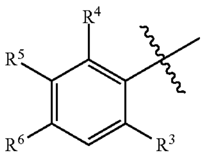

and optionally substituted five membered heteoaromatic ring containing one to three atoms selected from nitrogen and sulfur;

$R^3$ is selected from the group consisting of $C_{1-6}$ alkyl, $C_{1-6}$ alkoxy, $C_{1-6}$ haloalkyl, $C_{1-6}$ haloalkoxy, halogen, and —$CONR^{9a}R^{9b}$;

$R^4$ is selected from the group consisting of hydrogen, $C_{1-6}$ alkyl, $C_{1-6}$ alkoxy, $C_{1-6}$ haloalkyl, $C_{1-6}$ haloalkoxy, halogen, and —$CONR^{9a}R^{9b}$;

$R^5$ is selected from the group consisting of hydrogen,

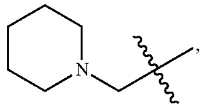,
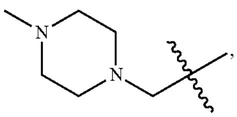,
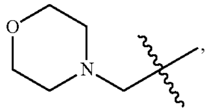,
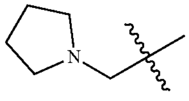,
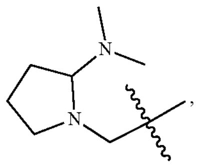,
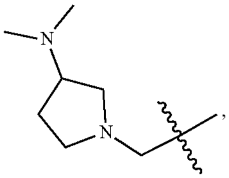,

-continued
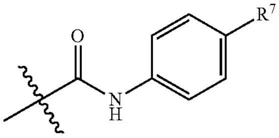
, and
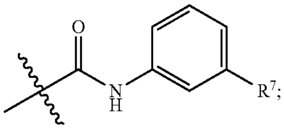
;
$R^6$ is selected from the group consisting of hydrogen, halogen,
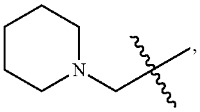
,
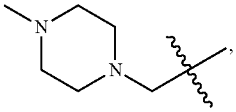
,
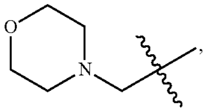
,
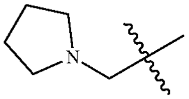
,
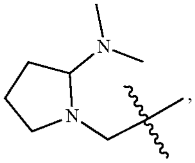
,
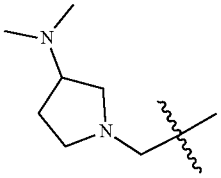
,
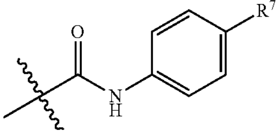
, and
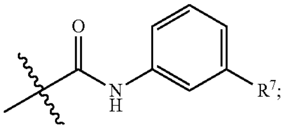
;
$R^7$ is selected from the group consisting of hydrogen,
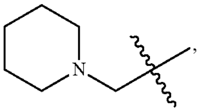
,
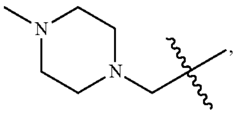
,
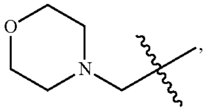
,
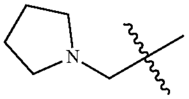
,
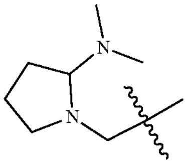
,
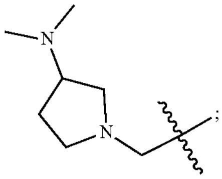
;
$R^{9a}$ is selected from the group consisting of hydrogen and $C_{1-6}$ alkyl;
and $R^{9b}$ is selected from the group consisting of hydrogen and $C_{1-6}$ alkyl;
The following compounds are outside the scope of the invention:
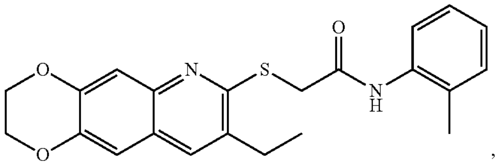
,
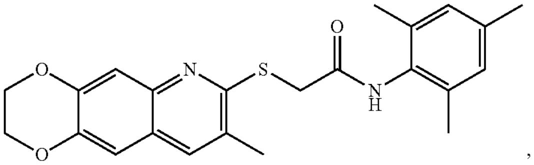
,
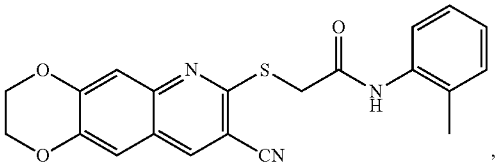
,
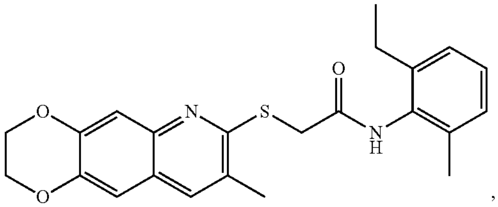
,
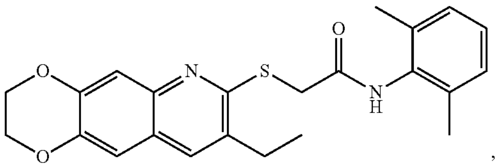
,
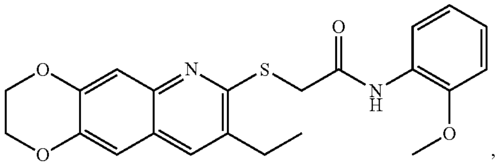
,
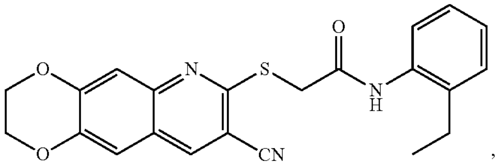
,
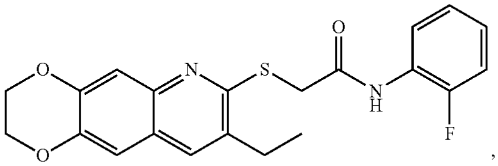
,
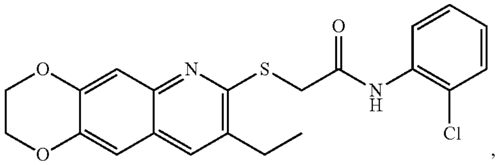
, -continued
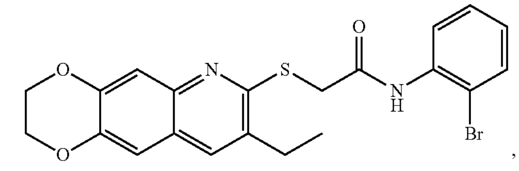,
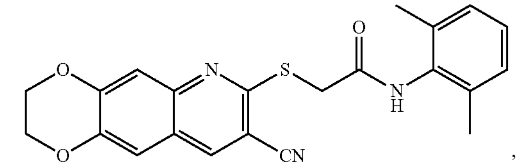,
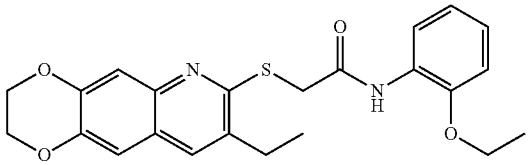,
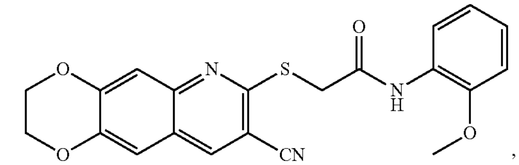,
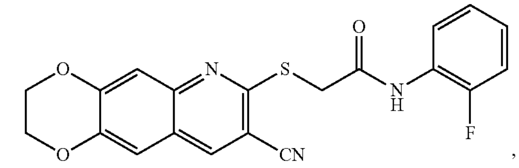,
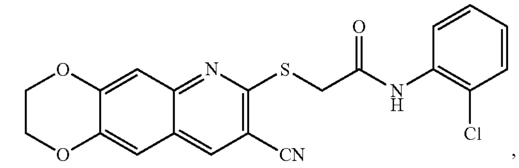,
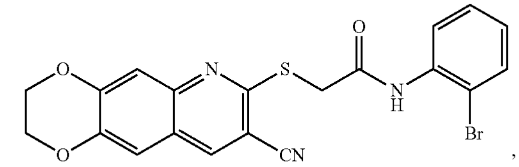,
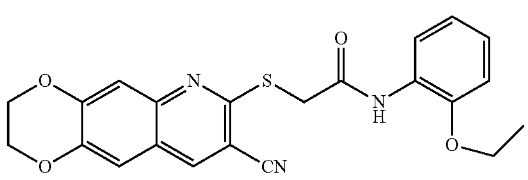,
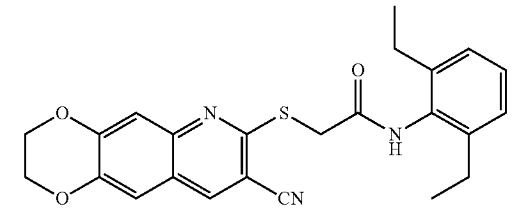,
-continued
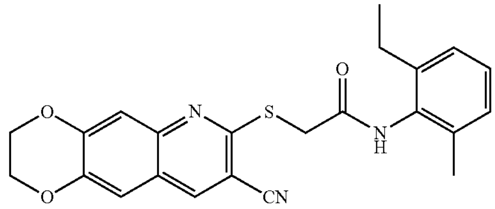,
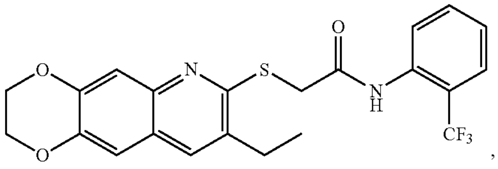, and
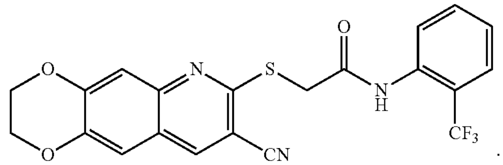.
In a preferred embodiment, $R^2$ is selected from the group consisting of
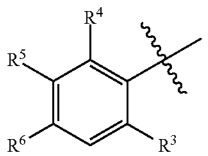,
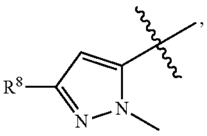,
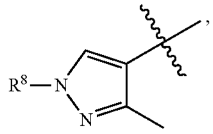,
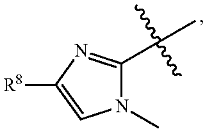,
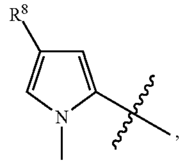,
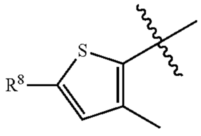,
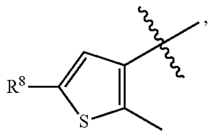,
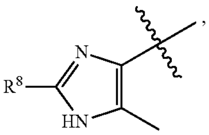,
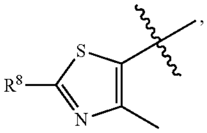,
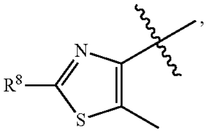, and
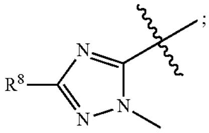;
$R^8$ is selected from the group consisting of hydrogen, $C_{1-6}$ alkyl, $C_{1-6}$ haloalkyl, $C_{3-7}$ branched alkyl, and $C_{3-7}$ cycloalkyl.

The compounds of the present invention include compounds having formula (I):

(II)

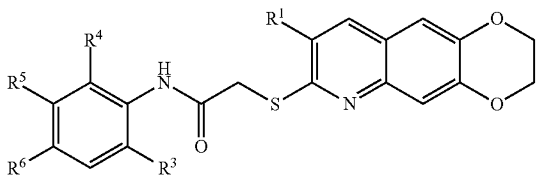

including enantiomers, diastereomers, tautomers, hydrates, solvates, pharmaceutically acceptable salts, and complexes thereof.

The compounds of the present invention include compounds having formula (III):

(III)

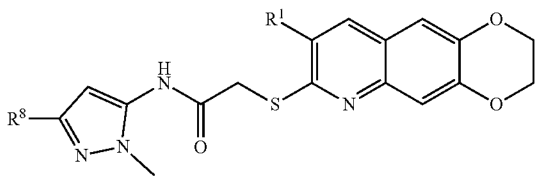

including enantiomers, diastereomers, tautomers, hydrates, solvates, pharmaceutically acceptable salts, and complexes thereof.

The compounds of the present invention include compounds having formula (IV):

(IV)

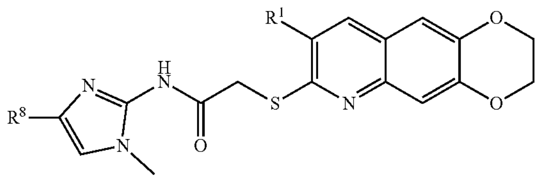

including enantiomers, diastereomers, tautomers, hydrates, solvates, pharmaceutically acceptable salts, and complexes thereof.

The compounds of the present invention include compounds having formula (V):

(V)

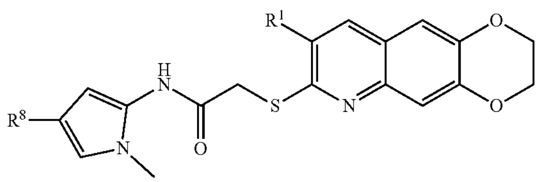

including enantiomers, diastereomers, tautomers, hydrates, solvates, pharmaceutically acceptable salts, and complexes thereof.

The compounds of the present invention include compounds having formula (VI):

(VI)

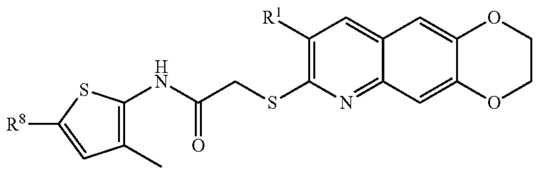

including enantiomers, diastereomers, tautomers, hydrates, solvates, pharmaceutically acceptable salts, and complexes thereof.

The compounds of the present invention include compounds having formula (VII):

(VII)

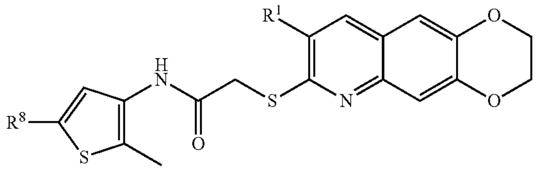

including enantiomers, diastereomers, tautomers, hydrates, solvates, pharmaceutically acceptable salts, and complexes thereof.

The compounds of the present invention include compounds having formula (VIII):

(VIII)

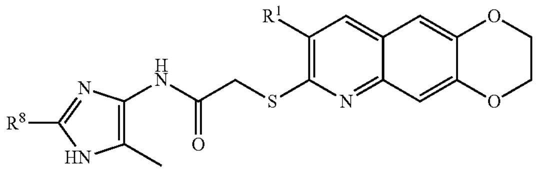

including enantiomers, diastereomers, tautomers, hydrates, solvates, pharmaceutically acceptable salts, and complexes thereof.

The compounds of the present invention include compounds having formula (IX):

(IX)

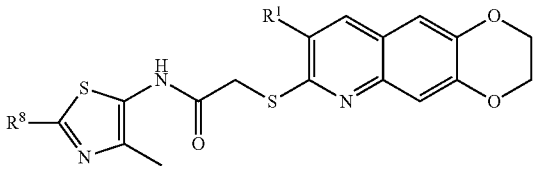

including enantiomers, diastereomers, tautomers, hydrates, solvates, pharmaceutically acceptable salts, and complexes thereof.

The compounds of the present invention include compounds having formula (X):

(X)

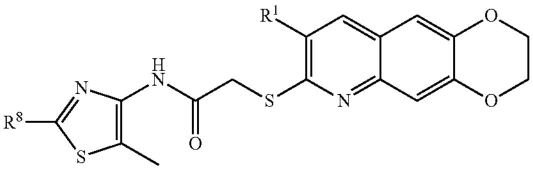

including enantiomers, diastereomers, tautomers, hydrates, solvates, pharmaceutically acceptable salts, and complexes thereof.

The compounds of the present invention include compounds having formula (XI):

(XI)

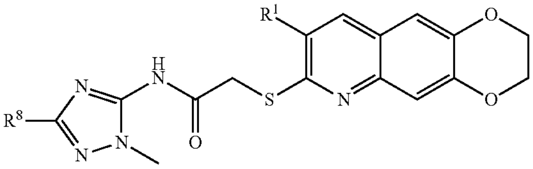

including enantiomers, diastereomers, tautomers, hydrates, solvates, pharmaceutically acceptable salts, and complexes thereof.

The compounds of the present invention include compounds having formula (XII):

(XII)

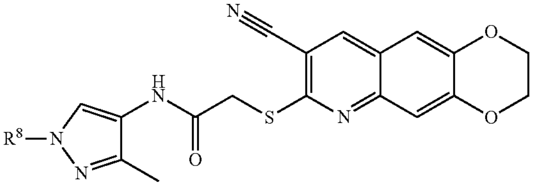

including enantiomers, diastereomers, tautomers, hydrates, solvates, pharmaceutically acceptable salts, and complexes thereof.

In a preferred embodiment, $R^8$ is selected from the group consisting of hydrogen, methyl, trifluoromethyl, ethyl, isopropyl, cyclopropyl, and t-butyl, In a preferred embodiment, $R^3$ is selected from the group consisting of —$CH_3$, —$OCH_3$, —$CF_3$, —$OCF_3$, —$CONHR^{9b}$,

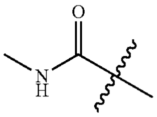, and halogen.

In a preferred embodiment, $R^4$ is selected from the group consisting of hydrogen, —$CH_3$, —$OCH_3$, —$CF_3$, —$OCF_3$, —$CONH^{9b}$,

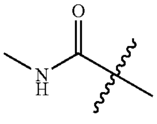, and halogen.

In a preferred embodiment, $R^8$ is selected from the group consisting of hydrogen, methyl, trifluoromethyl, ethyl, isopropyl, cyclopropyl, and t-butyl.

In a preferred embodiment of compounds of the formula (I), (I)

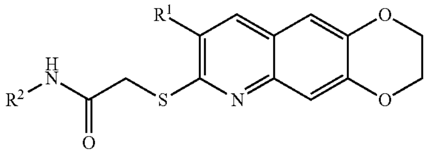

$R^1$ is selected from the group consisting of —$CH_3$, —$CH_2CH_3$, and nitrile;

$R^2$ is selected from the group consisting of

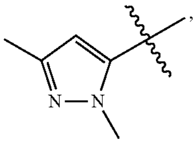, 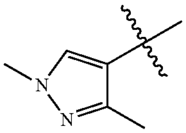,

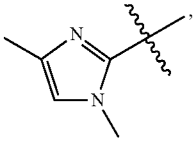, 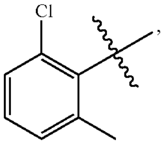,

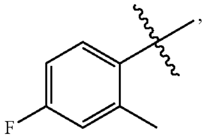, 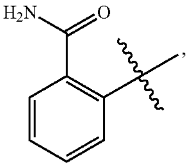,

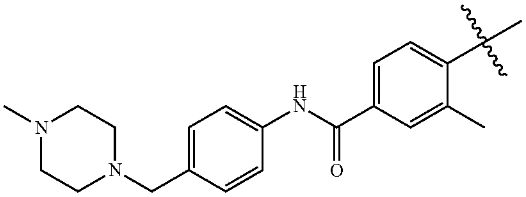,

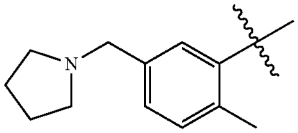, and

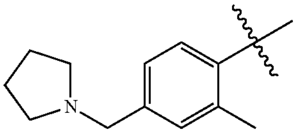

-continued

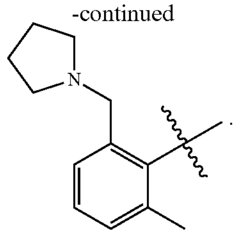

The present invention further relates to compositions comprising:
an effective amount of one or more compounds according to the present invention and an excipient.

The present invention also relates to a method for treating or preventing diseases that involve BCR-ABL kinase activity, including, for example, cancer, said method comprising administering to a subject an effective amount of a compound or composition according to the present invention.

The present invention yet further relates to a method for treating or preventing diseases that involve BCR-ABL kinase activity, including, for example, cancer, wherein said method comprises administering to a subject a composition comprising an effective amount of one or more compounds according to the present invention and an excipient.

The present invention also relates to a method for treating or preventing diseases that involve BCR-ABL kinase activity, including, for example, cancer, said method comprising administering to a subject an effective amount of a compound or composition according to the present invention wherein said cancer is selected from the group consisting of chronic myeloid leukemia, acute lymphoblastic leukemia, acute myeloid leukemia, chronic lymphocytic leukemia, multiple myeloma, lymphomas, and metastatic carcinoma.

The present invention yet further relates to a method for treating or preventing diseases that involve BCR-ABL kinase activity, including, for example, cancer, wherein said method comprises administering to a subject a composition comprising an effective amount of one or more compounds according to the present invention and an excipient wherein said cancer is selected from the group consisting of chronic myeloid leukemia, acute lymphoblastic leukemia, acute myeloid leukemia, chronic lymphocytic leukemia, multiple myeloma, lymphomas, and metastatic carcinoma.

The present invention also relates to a method for treating or preventing disease or conditions associated with cancer, and diseases that involve BCR-ABL kinase activity. Said methods comprise administering to a subject an effective amount of a compound or composition according to the present invention.

The present invention yet further relates to a method for treating or preventing disease or conditions associated with cancer, and diseases that involve BCR-ABL kinase activity, wherein said method comprises administering to a subject a composition comprising an effective amount of one or more compounds according to the present invention and an excipient.

The present invention also relates to a method for treating or preventing disease or conditions associated with BCR-ABL kinase activity. Said methods comprise administering to a subject an effective amount of a compound or composition according to the present invention.

The present invention yet further relates to a method for treating or preventing disease or conditions associated with BCR-ABL kinase activity, wherein said method comprises administering to a subject a composition comprising an effective amount of one or more compounds according to the present invention and an excipient.

The present invention further relates to a process for preparing the kinase inhibitors of the present invention.

These and other objects, features, and advantages will become apparent to those of ordinary skill in the art from a reading of the following detailed description and the appended claims. All percentages, ratios and proportions herein are by weight, unless otherwise specified.

All temperatures are in degrees Celsius (° C.) unless otherwise specified. All documents cited are in relevant part, incorporated herein by reference; the citation of any document is not to be construed as an admission that it is prior art with respect to the present invention.

BRIEF DESCRIPTION OF THE DRAWINGS

FIG. 3(*b*) shows a graph of the relative survival rate of chronic myeloid leukemia cells of cell lines K562-T315I and Ba/F3-T315I relative to the control, which is DMSO without the kinase inhibitor compound, as a function of the dose of the kinase inhibitor compound for kinase inhibitor compound AP-R234.

FIG. 3(*c*) shows a graph of the relative survival rate of chronic myeloid leukemia cells of cell lines K562-T315I and Ba/F3-T315I relative to the control, which is DMSO without the kinase inhibitor compound, as a function of the dose of the kinase inhibitor compound for kinase inhibitor compound AP-R235.

FIG. 3(*d*) shows a graph of the relative survival rate of chronic myeloid leukemia cells of cell line K562-T315I relative to the control, which is DMSO without the kinase inhibitor compound, as a function of the dose of the kinase inhibitor compound for kinase inhibitor compound AP-R357.

FIG. 3(*e*) shows a graph of the relative survival rate of chronic myeloid leukemia cells of cell line BV173-T315I relative to the control, which is DMSO without the kinase inhibitor compound, as a function of the dose of the kinase inhibitor compound for kinase inhibitor compound AP-R357.

FIG. 3(*f*) shows a graph of the relative survival rate of chronic myeloid leukemia cells of cell line Ba/F3-T315I relative to the control, which is DMSO without the kinase inhibitor compound, as a function of the dose of the kinase inhibitor compound for kinase inhibitor compound AP-R357.

DETAILED DESCRIPTION OF THE INVENTION

Figure 1:
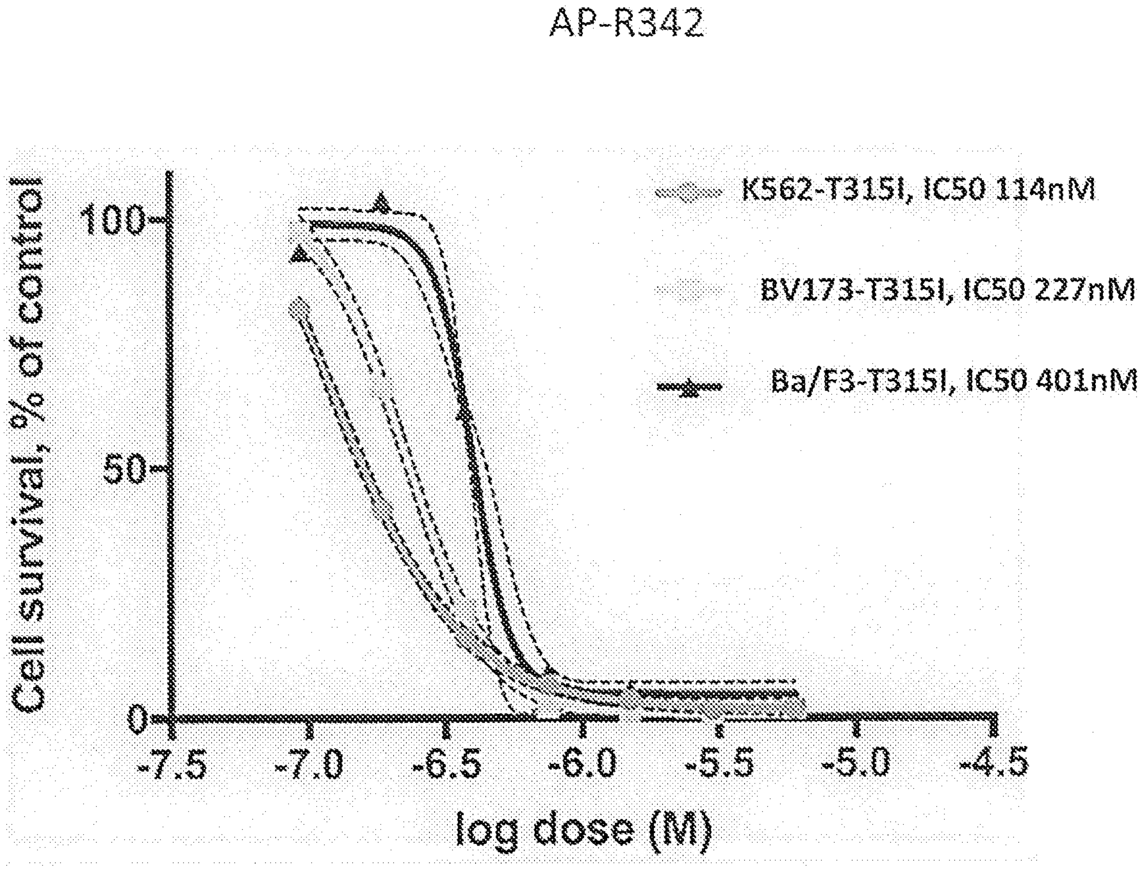
FIG. 1 shows a graph of the relative survival rate of chronic myeloid leukemia cells of cell lines K562-T315I, BV173-T315I, and Ba/F3-T315I relative to the control, which is DMSO without the kinase inhibitor compound, as a function of the dose of the kinase inhibitor compound for kinase inhibitor compound AP-R342.

The kinase inhibitors of the present invention are capable of treating and preventing diseases associated with BCR-ABL kinase activity, for example cancer. It has been discovered that the compounds the present disclosure are capable of inhibiting BCR-ABL kinase activity. It has further been discovered that the compounds of the disclosure are capable of treating or preventing diseases and conditions that involve BCR-ABL kinase activity including cancer. In addition, it has also been discovered that the compounds of the present disclosure are useful as cytotoxic agents capable of treating or preventing disease such as cancer. The compounds of the disclosure are capable of treating or preventing cancer including cancers selected from the group consisting of chronic myeloid leukemia, acute lymphoblastic leukemia, acute myeloid leukemia, chronic lymphocytic leukemia, multiple myeloma, lymphomas, and metastatic carcinoma.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1\_6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, isobutyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1\text{-}6}alkyl)_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo [3.1.1]heptanyl, 1,3-dimethyl[2.2.1]heptan-2-yl, bicyclo [2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., $—CF_3$, $—CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino) phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

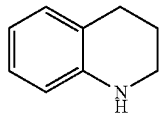

is, for the purposes of the present invention, considered a heterocyclic unit. 6,7-Dihydro-5H-cyclopentapyrimidine having the formula:

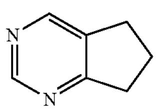

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

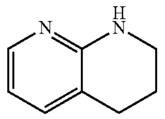

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, $—NO_2$, oxo (═O), $—OR^{10}$, —SR, $—N(R)_2$, $—NR^{10}C(O)R^{10}$, $—SO_2R^{10}$, $—SO_2OR^{10}$, $—SO_2N(R^{10})_2$, $—C(O)R^{10}$, $—C(O)OR^{10}$, $—C(O)N(R^{10})_2$, $C_{1-6}$ alkyl, $C_{1-6}$ haloalkyl, $C_{1-6}$ alkoxy, $C_{2-8}$ alkenyl, $C_{2-8}$ alkynyl, $C_4$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, $—NO_2$, oxo, and $R^{10}$; wherein $R^{10}$, at each occurrence, independently is hydrogen, $—OR^{11}$, $—SR^{11}$, $—C(O)R^{11}$, $—C(O)OR^{11}$, $—C(O)N(R^{11})_2$, $—SO_2R^{11}$, $—S(O)_2OR^{11}$, $—N(R^{11})_2$, $—NR^{11}C(O)R^{11}$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{10}$ units taken together with the atom(s) to which they are bound form an optionally substituted carbocycle or heterocycle wherein said carbocycle or heterocycle has 3 to 7 ring atoms; wherein $R^{11}$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two $R^{11}$ units taken together with the atom(s) to which they are bound form an optionally substituted carbocycle or heterocycle wherein said carbocycle or heterocycle preferably has 3 to 7 ring atoms.

In some embodiments, the substituents are selected from i) $—OR^{12}$; for example, —OH, $—OCH_3$, $—OCH_2CH_3$, $—OCH_2CH_2CH_3$;

ii) $—C(O)R^{12}$; for example, $—COCH_3$, $—COCH_2CH_3$, $—COCH_2CH_2CH_3$;

iii) $—C(O)OR^2$; for example, $—CO_2CH_3$, $—CO_2CH_2CH_3$, $—CO_2CH_2CH_2CH_3$;

iv) $—C(O)N(R^{12})_2$; for example, $—CONH_2$, $—CONHCH_3$, $—CON(CH_3)_2$;

v) $—N(R^{12})_2$; for example, $—NH_2$, $—NHCH_3$, $—N(CH_3)_2$, $—NH(CH_2CH_3)$;

vi) halogen: —F, —Cl, —Br, and —I;

vii) $—CH_eX_g$; wherein X is halogen, m is from 0 to 2, e+g=3; for example, $—CH_2F$, $—CHF_2$, $—CF_3$, $—CCl_3$, or $—CBr_3$;

viii) $—SO_2R^{12}$; for example, $—SO_2H$; $—SO_2CH_3$; $—SO_2C_6H_5$;

ix) $C_1$-$C_6$ linear, branched, or cyclic alkyl;

x) Cyano xi) Nitro;

xii) $N(R^{12})C(O)R^{12}$;

xiii) Oxo (═O);

xiv) Heterocycle; and xv) Heteroaryl.

wherein each $R^1$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g. optionally substituted $C_3$-$C_4$ cycloalkyl); or two $R^{12}$ units can be taken together to form a ring comprising 3-7 ring atoms. In certain aspects, each $R^{12}$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the compounds of the disclosure described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis.

The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^{11})_2$, each $R^{11}$ may be the same or different than the other). Combinations of substituents and/or variables are permissible only if such combinations result in stable compounds.

The terms “treat” and “treating” and “treatment” as used herein, refer to partially or completely alleviating, inhibiting, ameliorating and/or relieving a condition from which a patient is suspected to suffer.

As used herein, “therapeutically effective” and “effective dose” refer to a substance or an amount that elicits a desirable biological activity or effect.

Except when noted, the terms “subject” or “patient” are used interchangeably and refer to mammals such as human patients and non-human primates, as well as experimental animals such as rabbits, rats, and mice, and other animals. Accordingly, the term “subject” or “patient” as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Anticancer Agents

The kinase inhibitors of the present invention are cytotoxic anticancer and include all enantiomeric and diastereomeric forms and pharmaceutically accepted salts thereof having the formula (I):

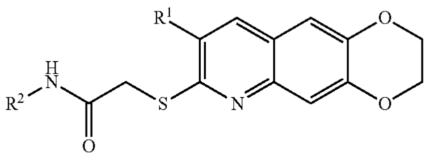

(I)

including enantiomers, diastereomers, tautomers, hydrates, solvates, pharmaceutically acceptable salts, and complexes thereof, wherein:

$R^1$ is selected from the group consisting of $C_{1-6}$ alkyl and nitrile;

$R^2$ is selected from the group consisting of

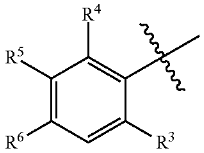

and optionally substituted five membered heteoaromatic ring containing one to three atoms selected from nitrogen and sulfur;

$R^3$ is selected from the group consisting of $C_{1-6}$ alkyl, $C_{1-6}$ alkoxy, $C_{1-6}$ haloalkyl, $C_{1-6}$ haloalkoxy, halogen, and —$CONR^{9a}R^{9b}$;

$R^4$ is selected from the group consisting of hydrogen, $C_{1-6}$ alkyl, $C_{1-6}$ alkoxy, $C_{1-6}$ haloalkyl, $C_{1-6}$ haloalkoxy, halogen, and —$CONR^{9a}R^{9b}$;

R is selected from the group consisting of hydrogen,

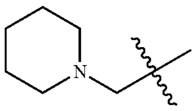, 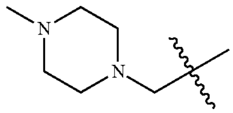,

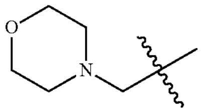, 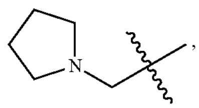,

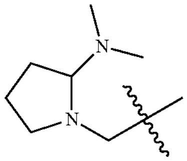, 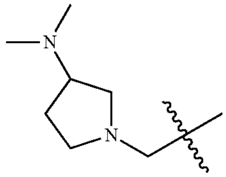,

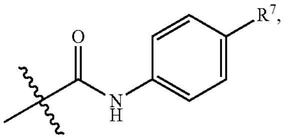, and

-continued
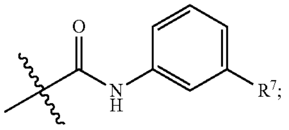
$R^6$ is selected from the group consisting of hydrogen, halogen,
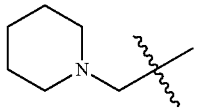, 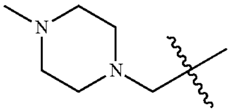,
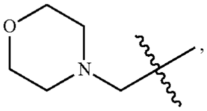, 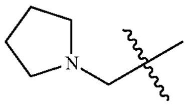,
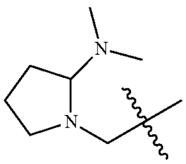, 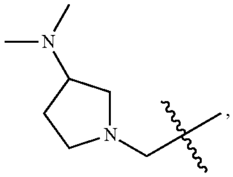,
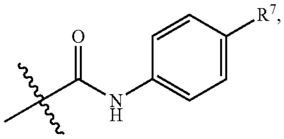 and
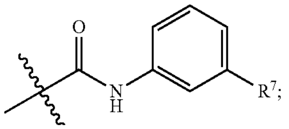
$R^7$ is selected from the group consisting of hydrogen,
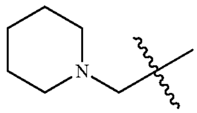, 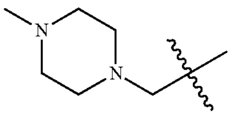,
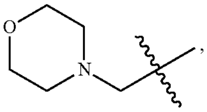, 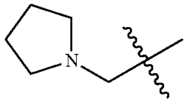,
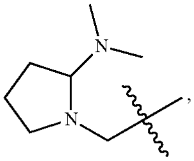, 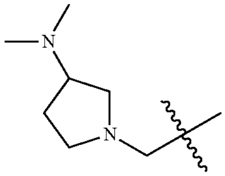;
$R^{9a}$ is selected from the group consisting of hydrogen and $C_{1-6}$ alkyl;
and $R^{9b}$ is selected from the group consisting of hydrogen and $C_{1-6}$ alkyl;
The following compounds are outside the scope of the invention:
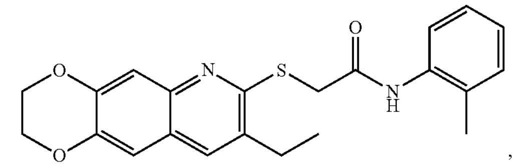,
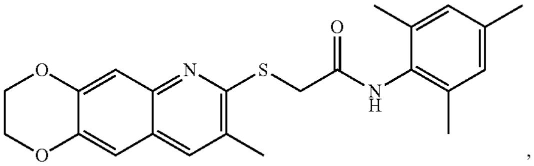,
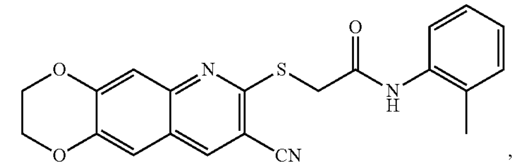,
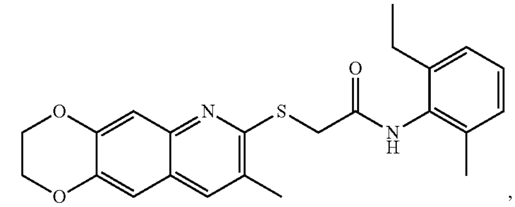,
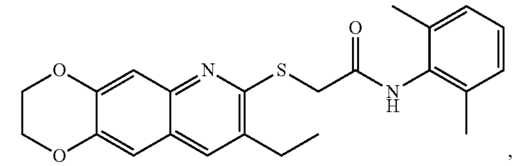,
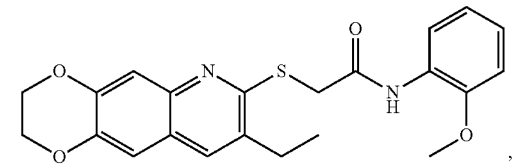,
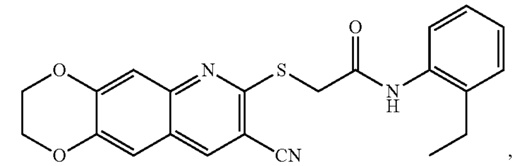,
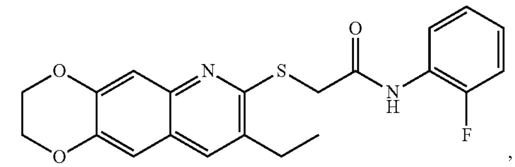,
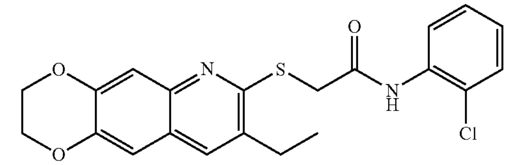,
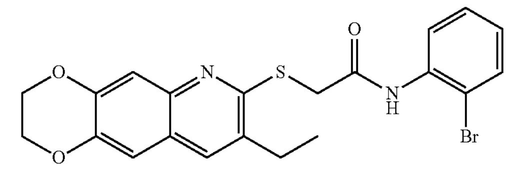, -continued

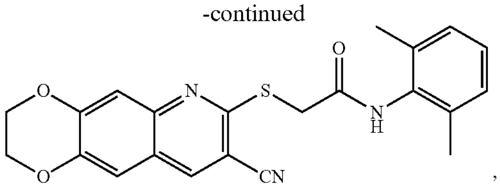,

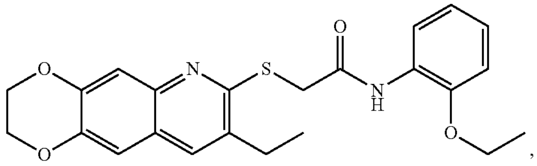,

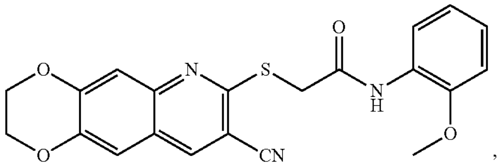,

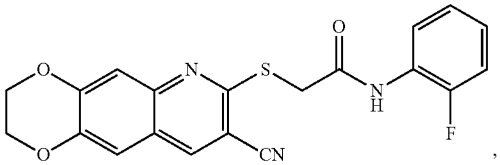,

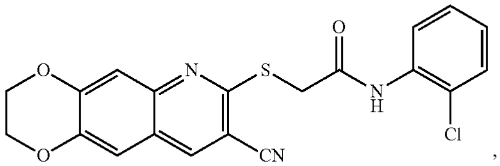,

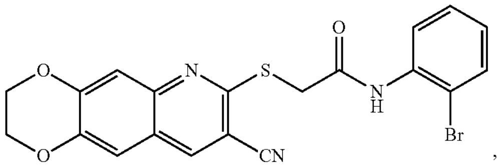,

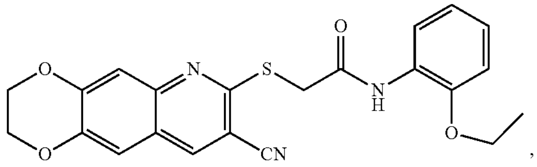,

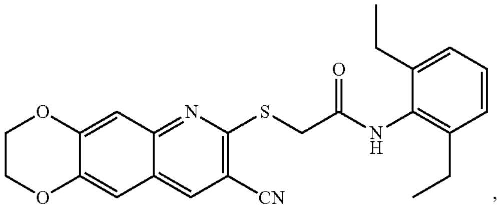,

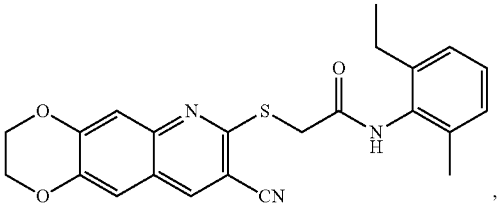,

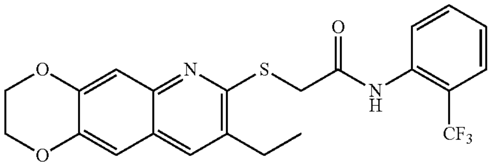, and

-continued

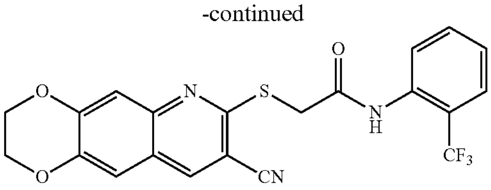.

In a preferred embodiment, $R^2$ is selected from the group consisting of

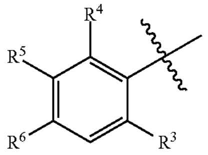,
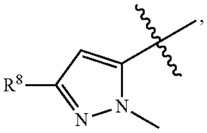,
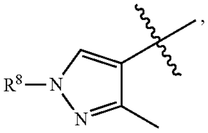,
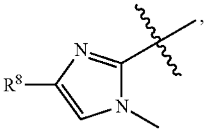,
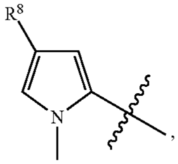,
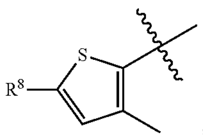,
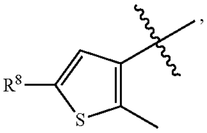,
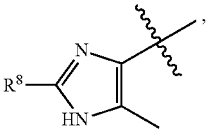,
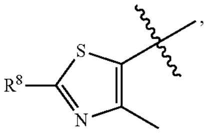,
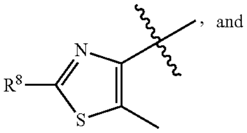, and
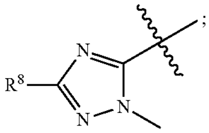;

$R^8$ is selected from the group consisting of hydrogen, $C_{1-6}$ alkyl, $C_{1-6}$ haloalkyl, $C_{3-7}$ branched alkyl, and $C_{3-7}$ cycloalkyl.

The compounds of the present invention include compounds having formula (II):

(II)

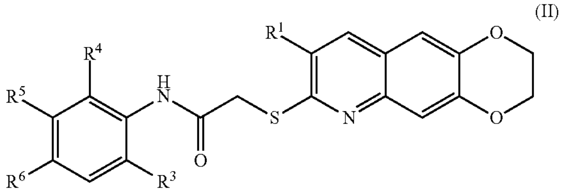

including enantiomers, diastereomers, tautomers, hydrates, solvates, pharmaceutically acceptable salts, and complexes thereof.

The compounds of the present invention include compounds having formula (III):

(III)

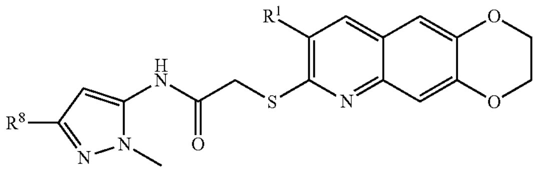

including enantiomers, diastereomers, tautomers, hydrates, solvates, pharmaceutically acceptable salts, and complexes thereof.

The compounds of the present invention include compounds having formula (IV):

(IV)

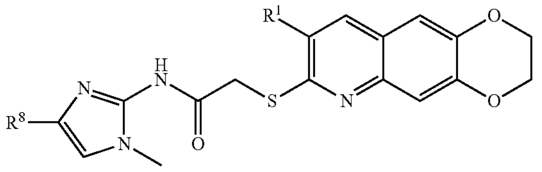

including enantiomers, diastereomers, tautomers, hydrates, solvates, pharmaceutically acceptable salts, and complexes thereof.

The compounds of the present invention include compounds having formula (V):

(V)

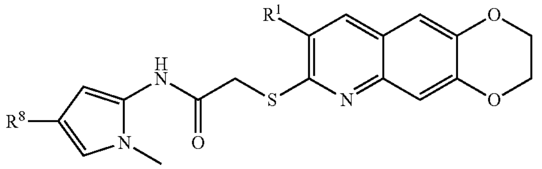

including enantiomers, diastereomers, tautomers, hydrates, solvates, pharmaceutically acceptable salts, and complexes thereof.

The compounds of the present invention include compounds having formula (VI):

(VI)

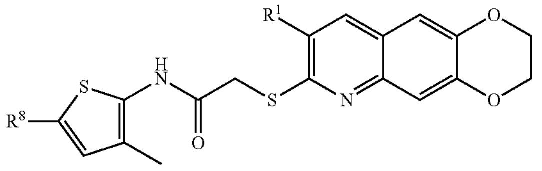

including enantiomers, diastereomers, tautomers, hydrates, solvates, pharmaceutically acceptable salts, and complexes thereof.

The compounds of the present invention include compounds having formula (VII):

(VII)

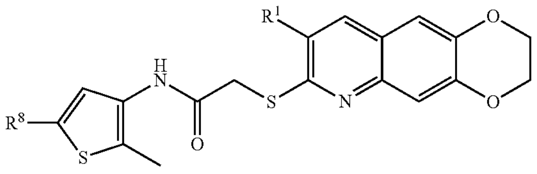

including enantiomers, diastereomers, tautomers, hydrates, solvates, pharmaceutically acceptable salts, and complexes thereof.

The compounds of the present invention include compounds having formula (VIII):

(VIII)

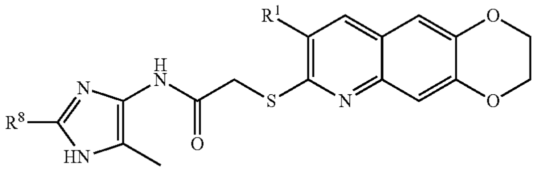

including enantiomers, diastereomers, tautomers, hydrates, solvates, pharmaceutically acceptable salts, and complexes thereof.

The compounds of the present invention include compounds having formula (IX):

(IX)

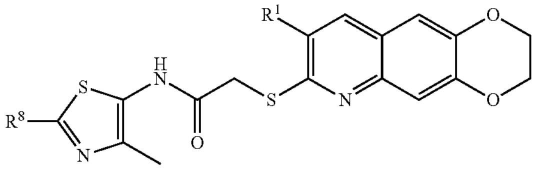

including enantiomers, diastereomers, tautomers, hydrates, solvates, pharmaceutically acceptable salts, and complexes thereof.

The compounds of the present invention include compounds having formula (X):

(X)

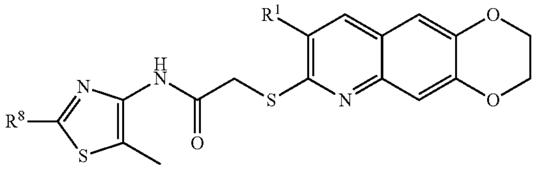

including enantiomers, diastereomers, tautomers, hydrates, solvates, pharmaceutically acceptable salts, and complexes thereof.

The compounds of the present invention include compounds having formula (XI):

(XI)

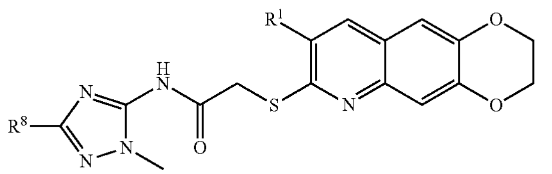

including enantiomers, diastereomers, tautomers, hydrates, solvates, pharmaceutically acceptable salts, and complexes thereof.

In a preferred embodiment, $R^8$ is selected from the group consisting of hydrogen, methyl, trifluoromethyl, ethyl, isopropyl, cyclopropyl, and t-butyl, In a preferred embodiment, $R^3$ is selected from the group consisting of $—CH_3$, $—OCH_3$, $—CF_3$, $—OCF_3$, $—CONHR^{9b}$,

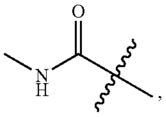 [SMILES: *C(=O)NC]

and halogen.

In a preferred embodiment, $R^4$ is selected from the group consisting of hydrogen, $—CH_3$, $—OCH_3$, $—CF_3$, $—OCF_3$, $—CONHR^{9b}$,

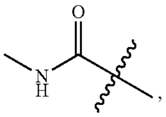 [SMILES: *C(=O)NC]

and halogen.

In a preferred embodiment, $R^8$ is selected from the group consisting of hydrogen, methyl, trifluoromethyl, ethyl, isopropyl, cyclopropyl, and t-butyl.

In a preferred embodiment of compounds of the formula (I), (I)

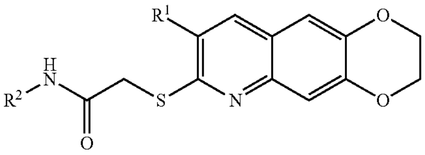

$R_1$ is selected from the group consisting of $—CH_3$, $—CH_2CH_3$, and nitrile;

$R_2$ is a suitably substituted phenyl ring or five-membered heterocyclic ring system as $R^2$ is selected from the group consisting of

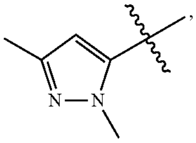

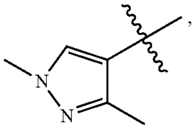

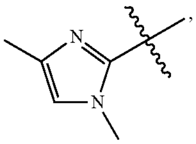

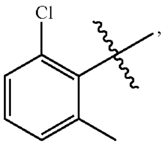

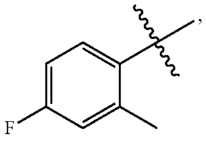

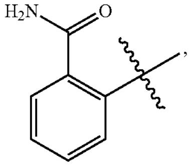

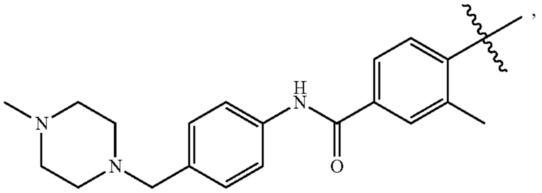

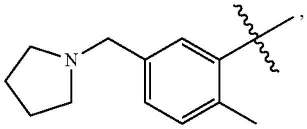

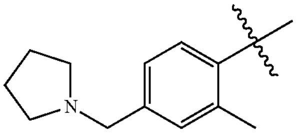

, and

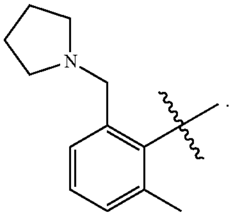

In some embodiments $R^1$ is $C_{1-6}$ alkyl.

In some embodiments $R^1$ is nitrile.

In some embodiments $R^1$ is $—CH_3$.

In some embodiments $R^1$ is $—CH_2CH_3$.

In some embodiments $R^2$ is

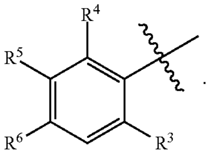

In some embodiments $R^2$ is optionally substituted five membered heteoaromatic ring containing one atom selected from nitrogen and sulfur.

In some embodiments $R_2$ is optionally substituted five membered heteoaromatic ring containing two atoms selected from nitrogen and sulfur.

In some embodiments $R^2$ is optionally substituted five membered heteoaromatic ring containing three atoms selected from nitrogen and sulfur.

In some embodiments $R^2$ is

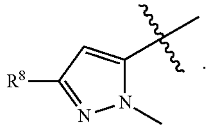

In some embodiments $R^2$ is

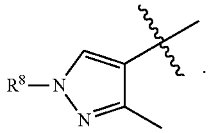

In some embodiments $R^2$ is

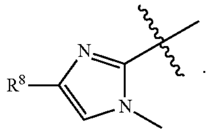

In some embodiments $R^2$ is

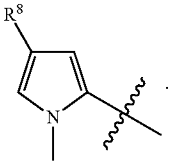

In some embodiments R is

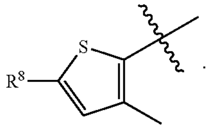

In some embodiments $R^2$ is

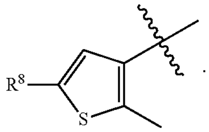

In some embodiments $R^2$ is

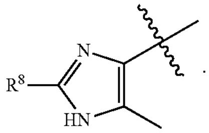

In some embodiments $R^2$ is

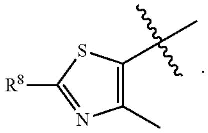

In some embodiments $R^2$ is

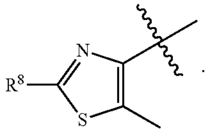

In some embodiments $R^2$ is

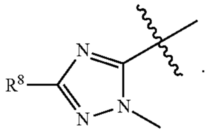

In some embodiments $R^2$ is

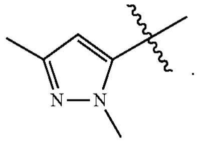 [SMILES: *c1cc(C)nn1C]

In some embodiments $R^2$ is

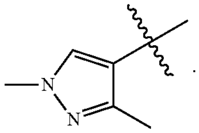 [SMILES: *c1cn(C)nc1C]

In some embodiments $R^2$ is

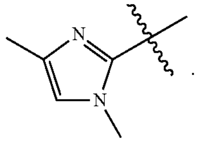 [SMILES: *c1nc(C)cn1C]

In some embodiments $R^2$ is

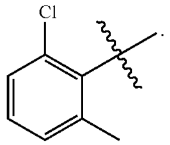 [SMILES: *c1c(C)cccc1Cl]

In some embodiments $R^2$ is

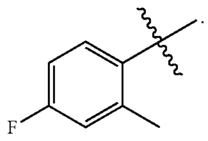 [SMILES: *c1ccc(F)cc1C]

In some embodiments $R^2$ is.

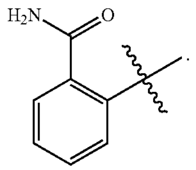

In some embodiments $R^2$ is

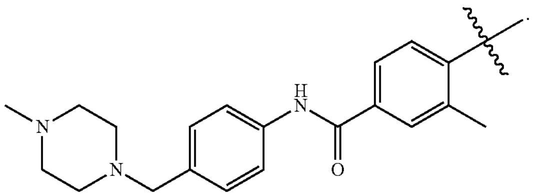 [SMILES: *c1ccc(C(=O)Nc2ccc(CN3CCN(C)CC3)cc2)cc1C]

In some embodiments $R_2$ is

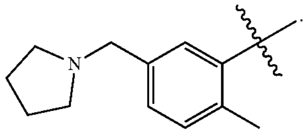 [SMILES: *c1cc(CN2CCCC2)ccc1C]

In some embodiments $R^2$ is

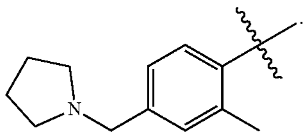 [SMILES: *c1ccc(CN2CCCC2)cc1C]

In some embodiments $R^2$ is

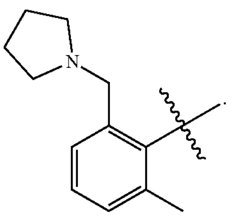 [SMILES: *c1c(C)cccc1CN1CCCC1]

In some embodiments $R_3$ is $C_1$ alkyl.
In some embodiments $R_3$ is $C_{1-6}$ alkoxy.
In some embodiments $R^3$ is $C_{1-6}$ haloalkyl.
In some embodiments $R^3$ is $C_{1-6}$ haloalkoxy.
In some embodiments $R_3$ is halogen.
In some embodiments $R^3$ is $—CONR^{9a}R^{9b}$.
In some embodiments $R^3$ is $—CH_3$.
In some embodiments $R_3$ is $—OCH_3$.
In some embodiments $R^3$ is $—CF_3$.
In some embodiments $R_3$ is $—OCF_3$.
In some embodiments $R_3$ is $—CONHR^{9b}$.
In some embodiments $R^3$ is

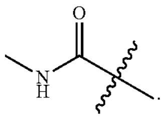 [SMILES: *C(=O)NC]

In some embodiments $R^4$ is hydrogen.
In some embodiments $R^4$ is $C_{1-6}$ alkyl.
In some embodiments $R^4$ is $C_{1-6}$ alkoxy.
In some embodiments $R^4$ is $C_{1-6}$ haloalkyl.
In some embodiments $R^4$ is $C_{1-6}$ haloalkoxy.
In some embodiments $R^4$ is halogen.
In some embodiments $R^4$ is $—CONR^{9a}R^{9b}$.
In some embodiments $R^4$ is $—CH_3$.
In some embodiments $R^4$ is $—OCH_3$.
In some embodiments $R^4$ is $—CF_3$.
In some embodiments $R^4$ is $—OCF_3$.
In some embodiments $R^4$ is $—CONHR^{9b}$.
In some embodiments $R^4$ is H

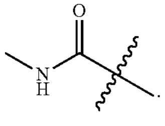 [SMILES: *C(=O)NC]

In some embodiments $R^5$ is hydrogen.
In some embodiments $R^5$ is

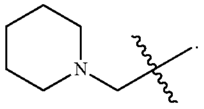 [SMILES: *CN1CCCCC1]

In some embodiments R is

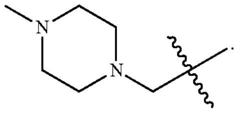 [SMILES: *CN1CCN(C)CC1]

In some embodiments R is

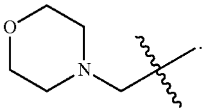 [SMILES: *CN1CCOCC1]

In some embodiments R is

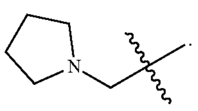 [SMILES: *CN1CCCC1]

In some embodiments $R^5$ is

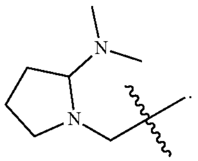 [SMILES: *CN1CCCC1N(C)C]

In some embodiments $R^5$ is

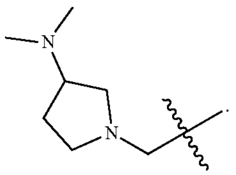 [SMILES: *CN1CCC(N(C)C)C1]

In some embodiments $R^5$ is

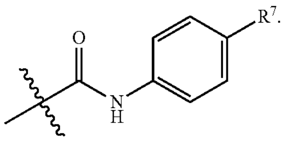

In some embodiments $R^5$ is

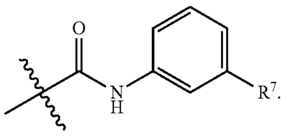

In some embodiments $R^6$ is hydrogen.
In some embodiments $R^6$ is halogen.
In some embodiments $R^6$ is

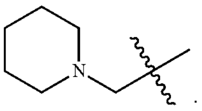 [SMILES: *CN1CCCCC1]

In some embodiments $R^6$ is

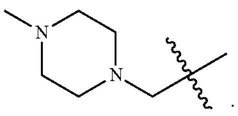 [SMILES: *CN1CCN(C)CC1]

In some embodiments $R^6$ is

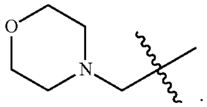 [SMILES: *CN1CCOCC1]

In some embodiments $R^6$ is

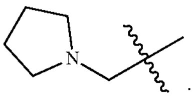 [SMILES: *CN1CCCC1]

In some embodiments $R^6$ is

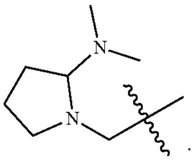 [SMILES: *CN1CCCC1N(C)C]

In some embodiments $R^6$ is

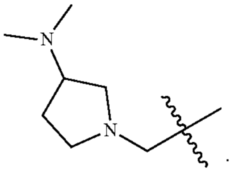 [SMILES: *CN1CCC(N(C)C)C1]

In some embodiments $R^6$ is

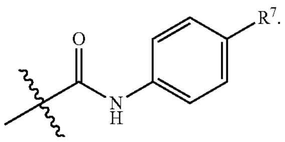

In some embodiments $R^6$ is

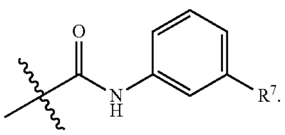

In some embodiments $R^7$ is hydrogen.
In some embodiments $R^7$ is

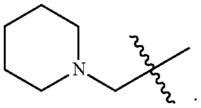 [SMILES: *CN1CCCCC1]

In some embodiments $R^7$ is

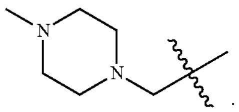 [SMILES: *CN1CCN(C)CC1]

In some embodiments $R^7$ is

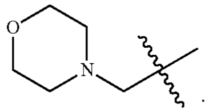 [SMILES: *CN1CCOCC1]

In some embodiments $R^7$ is

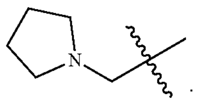 [SMILES: *CN1CCCC1]

In some embodiments $R^7$ is

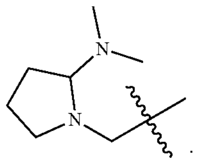

In some embodiments $R^7$ is

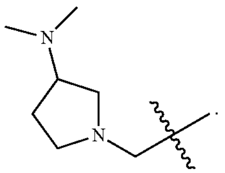 [SMILES: *CN1CCC(N(C)C)C1]

In some embodiments $R^8$ is hydrogen.
In some embodiments $R^8$ is $C_{1-6}$ alkyl.
In some embodiments $R^8$ is $C_{1-6}$ haloalkyl.
In some embodiments $R^8$ is $C_{3-7}$ branched alkyl.
In some embodiments $R^8$ is $C_{3-7}$ cycloalkyl.
In some embodiments $R^8$ is methyl.
In some embodiments $R^8$ is trifluoromethyl.
In some embodiments $R^8$ is ethyl.
In some embodiments $R^8$ is isopropyl.
In some embodiments $R^8$ is cyclopropyl.
In some embodiments $R^8$ is t-butyl.
In some embodiments $R^8$ is hydrogen.
In some embodiments $R^{9a}$ is $C_{1-6}$ alkyl.
In some embodiments $R^{9b}$ is hydrogen.
In some embodiments $R^{9b}$ is $C_{1-6}$ alkyl.

Compounds of the present invention include compounds having the formula (II) or a pharmaceutically acceptable salt form thereof:

(II)

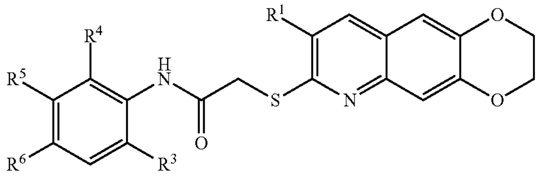

wherein non-limiting examples of $R^1$, $R^3$, $R^4$, $R^5$, and $R^6$ are defined herein below in Table I.

TABLE 1

| Exemplary compounds of the formula (II) | | | | | |
|---|---|---|---|---|---|
| Entry | $R^1$ | $R^3$ | $R^4$ | $R^5$ | $R^6$ |
| 1 | $CH_3$ | $CH_3$ | H | H | H |
| 2 | $CH_3$ | $CH_3$ | Cl | H | H |
| 3 | $CH_2CH_3$ | $CH_3$ | Cl | H | H |
| 4 | CN | $CH_3$ | Cl | H | H |
| 5 | $CH_3$ | $CH_3$ | H | H | F |
| 6 | $CH_2CH_3$ | $CH_3$ | H | H | F |
| 7 | CN | $CH_3$ | H | H | F |
| 8 | $CH_3$ | $—CONH_2$ | H | H | H |
| 9 | $CH_2CH_3$ | $—CONH_2$ | H | H | H |
| 10 | CN | $—CONH_2$ | H | H | H |
| 11 | $CH_3$ | $CH_3$ | H | 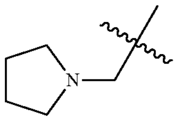 [SMILES: *CN1CCCC1] | H |
| 12 | $CH_2CH_3$ | $CH_3$ | H | 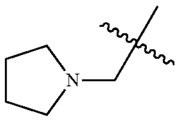 [SMILES: *CN1CCCC1] | H |

TABLE 1-continued

| Exemplary compounds of the formula (II) | | | | | |
|---|---|---|---|---|---|
| Entry | $R^1$ | $R^3$ | $R^4$ | $R^5$ | $R^6$ |
| 13 | CN | $CH_3$ | H | 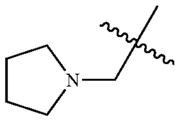 [SMILES: *CN1CCCC1] | H |
| 14 | $CH_3$ | $CH_3$ | H | H | 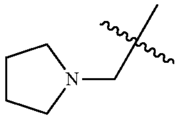 [SMILES: *CN1CCCC1] |
| 15 | $CH_2CH_3$ | $CH_3$ | H | H | 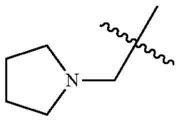 [SMILES: *CN1CCCC1] |
| 16 | CN | $CH_3$ | H | H | 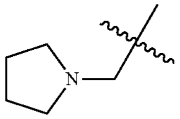 [SMILES: *CN1CCCC1] |

Compounds of the present invention include compounds having the formula (III) or a pharmaceutically acceptable salt form thereof:

(III)

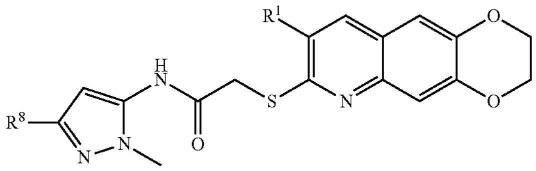

wherein non-limiting examples of $R^1$ and $R^8$ are defined herein below in Table 2.

TABLE 2

| Exemplary compounds of the formula (III) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |

TABLE 2-continued

| Exemplary compounds of the formula (III) | | |
|---|---|---|
| Entry | $R^1$ | $R^8$ |
| 20 | CN | t-butyl |
| 21 | CN | cyclopropyl |

Compounds of the present invention include compounds having the formula (IV) or a pharmaceutically acceptable salt form thereof:

(IV)

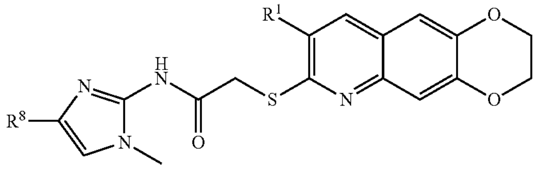

wherein non-limiting examples of $R^1$ and $R^8$ are defined herein below in Table 3.

TABLE 3

| Exemplary compounds of the formula (IV) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |

TABLE 3-continued

| Exemplary compounds of the formula (IV) | | |
|---|---|---|
| Entry | $R^1$ | $R^8$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (V) or a pharmaceutically acceptable salt form thereof:

(V)

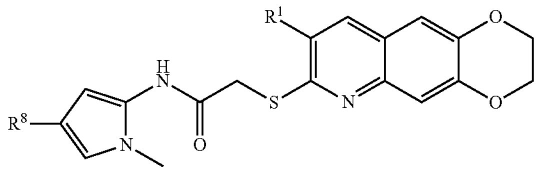

wherein non-limiting examples of $R^1$ and $R^8$ are defined herein below in Table 4.

TABLE 4

| Exemplary compounds of the formula (V) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (VI) or a pharmaceutically acceptable salt form thereof:

(VI)

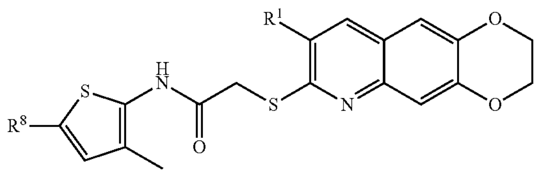

wherein non-limiting examples of $R^1$ and $R^8$ are defined herein below in Table 5.

TABLE 5

| Exemplary compounds of the formula (VI) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (VII) or a pharmaceutically acceptable salt form thereof:

(VII)

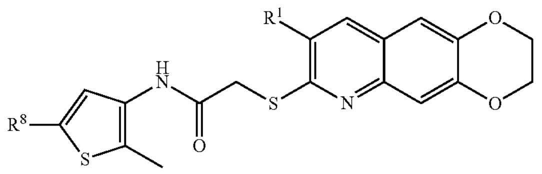

wherein non-limiting examples of $R^1$ and $R^8$ are defined herein below in Table 6.

TABLE 6

| Exemplary compounds of the formula (VII) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |

TABLE 6-continued

| Exemplary compounds of the formula (VII) | | |
|---|---|---|
| Entry | $R^1$ | $R^8$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (VIII) or a pharmaceutically acceptable salt form thereof:

(VIII)

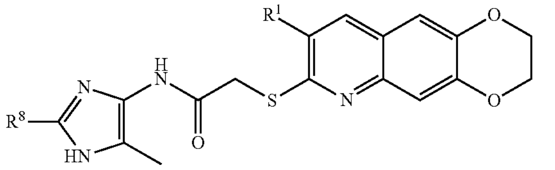

wherein non-limiting examples of $R^1$ and $R^8$ are defined herein below in Table 7.

TABLE 7

| Exemplary compounds of the formula (VIII) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (IX) or a pharmaceutically acceptable salt form thereof:

(IX)

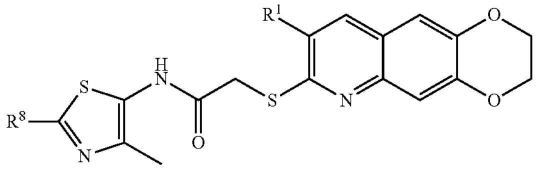

wherein non-limiting examples of $R^1$ and $R^8$ are defined herein below in Table 8.

TABLE 8

| Exemplary compounds of the formula (IX) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (X) or a pharmaceutically acceptable salt form thereof:

(X)

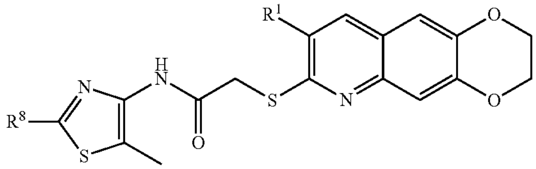

wherein non-limiting examples of $R^1$ and $R^8$ are defined herein below in Table 9.

TABLE 9

| Exemplary compounds of the formula (X) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |

TABLE 9-continued

| Exemplary compounds of the formula (X) | | |
|---|---|---|
| Entry | $R^1$ | $R^8$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (XI) or a pharmaceutically acceptable salt form thereof:

(XI)

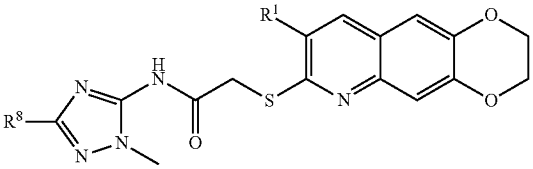

wherein non-limiting examples of $R^1$ and $R^8$ are defined herein below in Table 10.

TABLE 10

| Exemplary compounds of the formula (XI) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | Isopropyl |
| 5 | $CH_2CH_3$ | Isopropyl |
| 6 | CN | Isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (XII) or a pharmaceutically acceptable salt form thereof:

(XII)

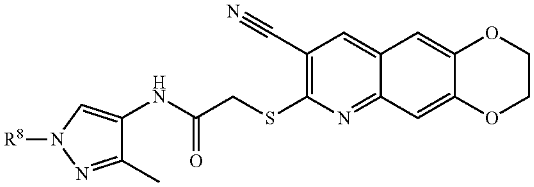

wherein non-limiting examples of $R^1$ and $R^8$ are defined herein below in Table 11.

TABLE 11

| Exemplary compounds of the formula (XII) | | |
|---|---|---|
| Entry | $R^1$ | $R^8$ |
| 1 | $CH_3$ | H |
| 2 | $CH_2CH_3$ | H |
| 3 | CN | H |
| 4 | $CH_3$ | isopropyl |
| 5 | $CH_2CH_3$ | isopropyl |
| 6 | CN | isopropyl |
| 7 | $CH_3$ | cyclopropyl |
| 8 | $CH_3$ | $CH_3$ |
| 9 | $CH_2CH_3$ | $CH_3$ |
| 10 | CN | $CH_3$ |
| 11 | $CH_3$ | $CH_2CH_3$ |
| 12 | $CH_2CH_3$ | $CH_2CH_3$ |
| 13 | CN | $CH_2CH_3$ |
| 14 | $CH_2CH_3$ | cyclopropyl |
| 15 | $CH_3$ | $CF_3$ |
| 16 | $CH_2CH_3$ | $CF_3$ |
| 17 | CN | $CF_3$ |
| 18 | $CH_3$ | t-butyl |
| 19 | $CH_2CH_3$ | t-butyl |
| 20 | CN | t-butyl |
| 21 | CN | cyclopropyl |

Compounds of the present invention include compounds having the formula (XIII) or a pharmaceutically acceptable salt form thereof:

(XIII)

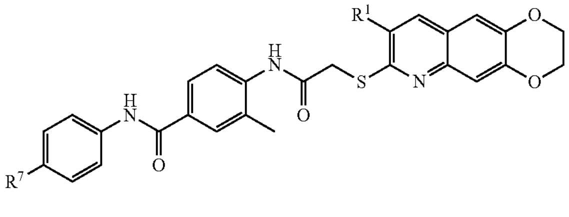

wherein non-limiting examples of R and R are defined herein below in Table 12.

TABLE 12

| Exemplary compounds of the formula (XIII) | | |
|---|---|---|
| Entry | $R^1$ | $R^8$ |
| 1 | $CH_3$ | 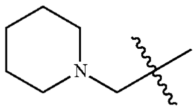 [SMILES: *CN1CCCCC1] |

TABLE 12-continued

| Exemplary compounds of the formula (XIII) | | |
|---|---|---|
| Entry | $R^1$ | $R^8$ |
| 2 | $CH_2CH_3$ | 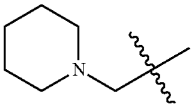 [SMILES: *CN1CCCCC1] |
| 3 | CN | 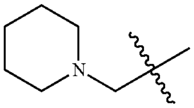 [SMILES: *CN1CCCCC1] |
| 4 | $CH_3$ | 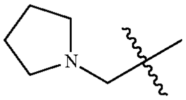 |
| 5 | $CH_2CH_3$ | 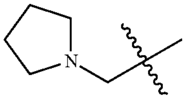 [SMILES: *CN1CCCC1] |
| 6 | CN | 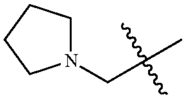 [SMILES: *CN1CCCC1] |
| 7 | $CH_3$ | 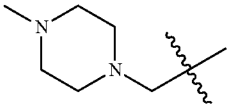 [SMILES: *CN1CCN(C)CC1] |
| 8 | $CH_2CH_3$ | 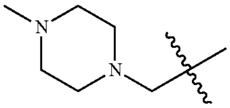 [SMILES: *CN1CCN(C)CC1] |
| 9 | CN | 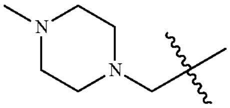 [SMILES: *CN1CCN(C)CC1] |
| 10 | $CH_3$ | 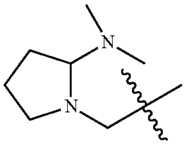 [SMILES: *CN1CCCC1N(C)C] |
| 11 | $CH_2CH_3$ | 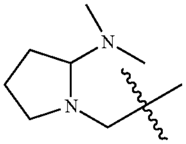 [SMILES: *CN1CCCC1N(C)C] |
| 12 | CN | 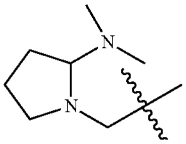 [SMILES: *CN1CCCC1N(C)C] |
| 13 | $CH_3$ | 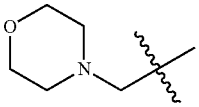 [SMILES: *CN1CCOCC1] |
| 14 | $CH_2CH_3$ | 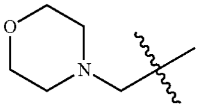 [SMILES: *CN1CCOCC1] |
| 15 | CN | 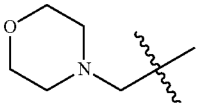 [SMILES: *CN1CCOCC1] |
| 16 | $CH_3$ | 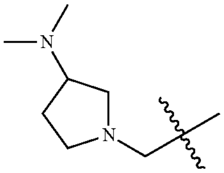 [SMILES: *CN1CCC(N(C)C)C1] |
| 17 | $CH_2CH_3$ | 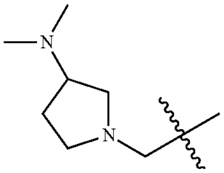 [SMILES: *CN1CCC(N(C)C)C1] |
| 18 | CN | 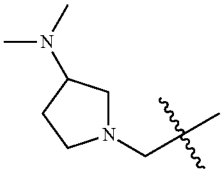 [SMILES: *CN1CCC(N(C)C)C1] |

Compounds of the present invention include compounds having the formula (XIV) or a pharmaceutically acceptable salt form thereof:

(XIV)

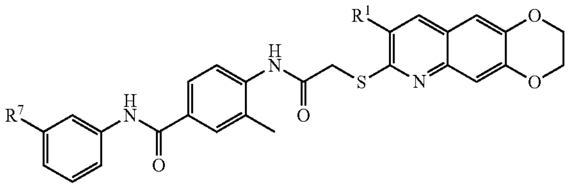

wherein non-limiting examples of $R^1$ and $R^7$ are defined herein below in Table 13.

TABLE 12

| Exemplary compounds of the formula (XIV) | | |
|---|---|---|
| Entry | $R^1$ | $R^8$ |
| 1 | $CH_3$ | 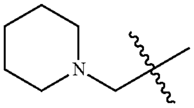 [SMILES: *CN1CCCCC1] |
| 2 | $CH_2CH_3$ | 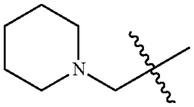 [SMILES: *CN1CCCCC1] |
| 3 | CN | 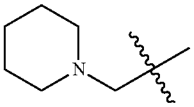 [SMILES: *CN1CCCCC1] |
| 4 | $CH_3$ | 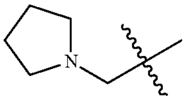 [SMILES: *CN1CCCC1] |
| 5 | $CH_2CH_3$ | 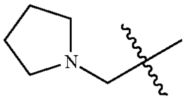 [SMILES: *CN1CCCC1] |
| 6 | CN | 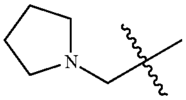 [SMILES: *CN1CCCC1] |
| 7 | $CH_3$ | 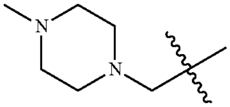 [SMILES: *CN1CCN(C)CC1] |
| 8 | $CH_2CH_3$ | 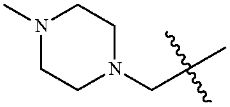 [SMILES: *CN1CCN(C)CC1] |
| 9 | CN | 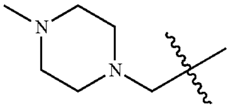 [SMILES: *CN1CCN(C)CC1] |
| 10 | $CH_3$ | 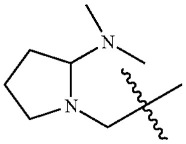 [SMILES: *CN1CCCC1N(C)C] |
| 11 | $CH_2CH_3$ | 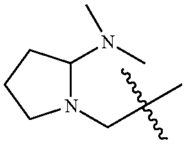 [SMILES: *CN1CCCC1N(C)C] |
| 12 | CN | 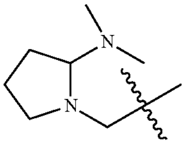 [SMILES: *CN1CCCC1N(C)C] |
| 13 | $CH_3$ | 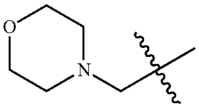 [SMILES: *CN1CCOCC1] |
| 14 | $CH_2CH_3$ | 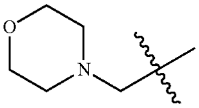 [SMILES: *CN1CCOCC1] |
| 15 | CN | 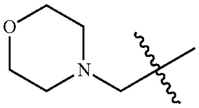 [SMILES: *CN1CCOCC1] |
| 16 | $CH_3$ | 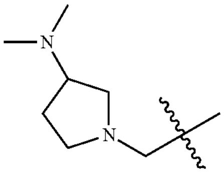 [SMILES: *CN1CCC(N(C)C)C1] |
| 17 | $CH_2CH_3$ | 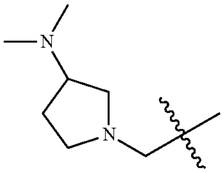 [SMILES: *CN1CCC(N(C)C)C1] |
| 18 | CN | 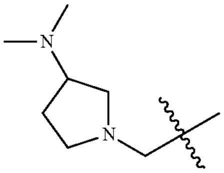 [SMILES: *CN1CCC(N(C)C)C1] |

For the purposes of demonstrating the manner in which the compounds of the present invention are named and referred-to-herein, the compound having the formula:

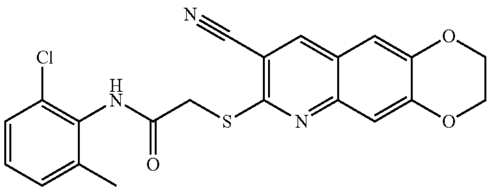 [SMILES: Cc1cccc(Cl)c1NC(=O)CSc1nc2cc3c(cc2cc1C#N)OCCO3]

has the chemical name N-(2-chloro-6-methylphenyl)-2-((8-cyano-2,3-dihydro-[1,4]dioxino[2,3-g]quinolin-7-yl)thio)acetamide.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the kinase inhibitors of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes.

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Scheme 1.

Scheme 1

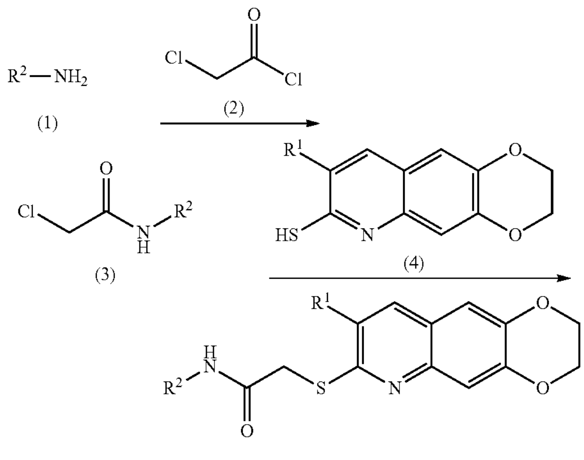

(5)

A compound of the formula (1), a known compound or a compound prepared by known methods, is reacted with a compound of the formula (2) in the presences of a base such as sodium hydroxide, lithium hydroxide, potassium hydroxide, barium hydroxide, sodium carbonate, potassium carbonate, lithium carbonate and the like, in the presence of a solvent such as methylene chloride, 1,2-dichloroethane, chloroform, 1,4-dioxane, tetrahydrofuran, acetonitrile, and the like, optionally in the presence of water, optionally with heating, optionally with microware irradiation to provide a compound of the formula (3). A compound of the formula (3) is reacted with a compound of the formula (4), a known compound or a compound prepared by known methods, in the presence of an acetate salt such as sodium acetate, lithium acetate, potassium acetate, tetrabutylammonium acetate, and the like, in the presence of a solvent such as methanol, ethanol, n-propanol, isopropanol, and the like, optionally with heating, optionally with microwave irradiation, to provide a compound of the formula (5)

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

Examples 1-14 provides methods for preparing representative compounds of formula (I). The skilled practitioner will know how to substitute the appropriate reagents, starting materials and purification methods known to those skilled in the art, in order to prepare additional compounds of the present invention.

Synthetic Procedure 1: Preparation of 2-Cl-Amides.

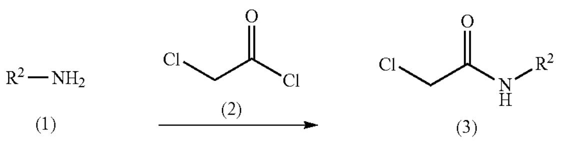

The respective amine (1) was stirred in 2N sodium hydroxide solution (1.5 ml per millimole of (1)) at 23° C., chloroacetyl chloride (2) (2.5% molar excess) in dichloromethane (DCM) (1.5 ml per millimole of aniline) was added gradually with vigorous stirring. The reaction mixture was stirred at room temperature for 2 hours, transferred to a separating funnel and the layers separated. The aqueous layer was further extracted with DCM (x2) and the combined organics washed with 1N HCl (x2), water (x2) and saturated brine (x2). After drying over $MgSO_4$ the DCM solution was evaporated to dryness and the isolated product (3) dried thoroughly under vacuum.

The following compounds for the example final compounds were prepared using this method Example 1: 2-chloro-N-(2-chloro-6-methylphenyl)acetamide

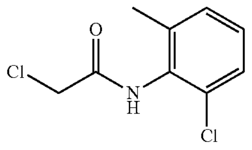

The title compound was prepared from chloroacetyl chloride and 2-chloro-6-methylaniline using the methods described in synthetic procedure 1.

Example 2: 2-chloro-N-(4-fluoro-2-methylphenyl)acetamide

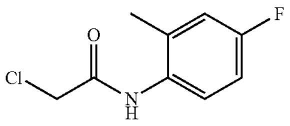

The title compound was prepared from chloroacetyl chloride and 4-fluoro-2-methylaniline using the methods described in synthetic procedure 1.

Example 3: 2-(2-chloroacetamido)benzamide

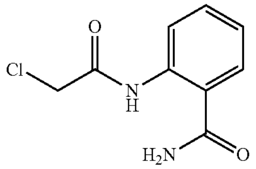 [SMILES: NC(=O)c1ccccc1NC(=O)CCl]

The title compound was prepared from chloroacetyl chloride and 2-aminobenzamide using the methods described in synthetic procedure 1.

Example 4: 4-(2-chloroacetamido)-3-methylbenzoic Acid

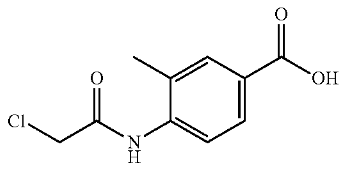

The title compound was prepared from chloroacetyl chloride and 4-amino-3-methylbenzoic acid using the methods described in synthetic procedure 1.

Example 5: 2-chloro-N-(1-methyl-1H-pyrazol-5-yl)acetamide

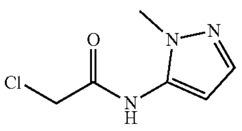

The title compound was prepared from chloroacetyl chloride and 1-methyl-H-pyrazol-5-amine using the methods described in synthetic procedure 1.

Example 6: 2-chloro-N-[2-methyl-5-(pyrrolidin-1-ylmethyl)phenyl]acetamide

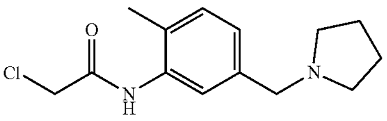 [SMILES: Cc1ccc(CN2CCCC2)cc1NC(=O)CCl]

The title compound was prepared from chloroacetyl chloride and 2-methyl-5-(pyrrolidin-1-ylmethyl)aniline using the methods described in synthetic procedure 1.

Synthetic Procedure 2: Preparation of Compounds of the Formula (5)

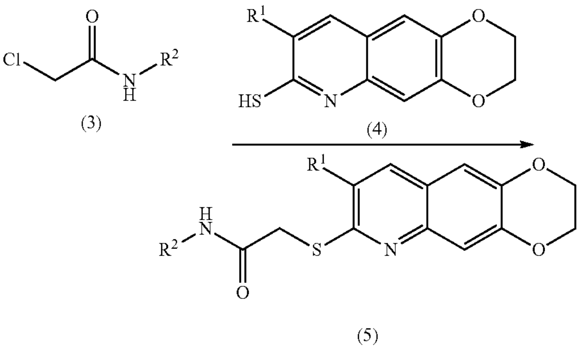

(5)

A compound of the formula (2) was combined with a compound of the formula (3)(5% molar excess) and sodium acetate (3 molar equivalents) in n-propanol (2 ml per millimole of chloroacetamide intermediate), the reaction was brought to reflux with stirring, after 3 hours the reaction was cooled, the product filtered off washing with small volumes of ice-cold propanol and further purified using methods known to one skilled in the art.

Example 7: Synthesis of N-(2-chloro-6-methylphenyl)-2-({8-cyano-2H,3H-[1,4]dioxino[2,3-g]quinolin-7-yl}sulfanyl)acetamide (AP-R342)

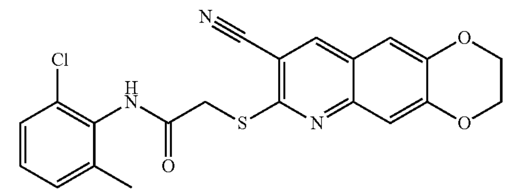 [SMILES: Cc1cccc(Cl)c1NC(=O)CSc1nc2cc3c(cc2cc1C#N)OCCO3]

The title compound was prepared from 7-sulfanyl-2H,3H-[1,4]dioxino[2,3-g]quinoline-8-carbonitrile and 2-chloro-N-(2-chloro-6-methylphenyl)acetamide using the method described in synthetic procedure 2. LCMS retention time 0.7 minutes, MS: 426.34 (M+H).

Example 8: Synthesis of 2-({8-cyano-2H,3H-[1,4]dioxino[2,3-g]quinolin-7-yl}sulfanyl)-N-(4-fluoro-2-methylphenyl)acetamide (AP-R343)

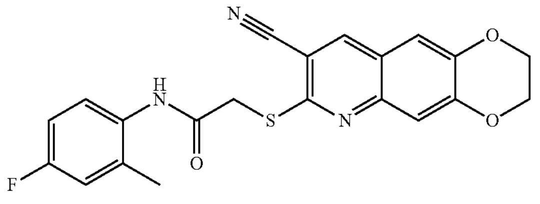 [SMILES: Cc1cc(F)ccc1NC(=O)CSc1nc2cc3c(cc2cc1C#N)OCCO3]

The title compound was prepared from 7-sulfanyl-2H,3H-[1,4]dioxino[2,3-g]quinoline-8-carbonitrile and 2-chloro-N-(4-fluoro-2-methylphenyl)acetamide using the method described in synthetic procedure 2. LCMS MS: 410.1 $(M+H)^+$.

Example 9: Synthesis of 2-[2-(8-cyano-2H,3H-[1,4]dioxino[2,3-g]quinolin-7-ylsulfanyl)acetamido]benzamide (AP-R230)

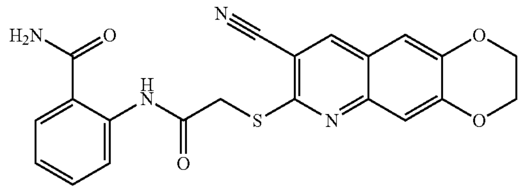 [SMILES: N#Cc1cc2cc3c(cc2nc1SCC(=O)Nc1ccccc1C(N)=O)OCCO3]

The title compound was prepared from 7-sulfanyl-2H,3H-[1,4]dioxino[2,3-g]quinoline-8-carbonitrile and 2-(2-chloroacetamido)benzamide using the method described in synthetic procedure 2. LCMS retention time 1.57 minutes, MS: 421 $(M+H)^+$.

Example 10: Synthesis of 4-[2-(8-cyano-2H,3H-[1,4]dioxino[2,3-g]quinolin-7-ylsulfanyl) acetamido]-3-methyl-N-4-[(4-methylpiperazin-1-yl)methyl]phenylbenzamide Hydrochloride (APR-234)

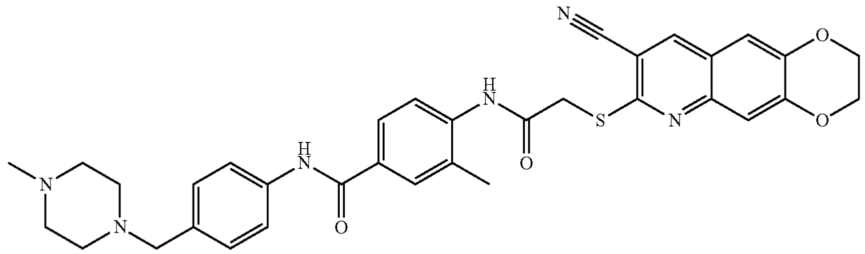 [SMILES: Cc1cc(C(=O)Nc2ccc(CN3CCN(C)CC3)cc2)ccc1NC(=O)CSc1nc2cc3c(cc2cc1C#N)OCCO3]

Step 1: Synthesis of 4-(2-chloroacetamido)-3-methyl-N-{4-[(4-methylpiperazin-1-yl)methyl]phenyl}benzamide: 4-(2-chloroacetamido)-3-methylbenzoic acid was converted to the 4-(2-chloroacetamido)-3-methylbenzoyl chloride using $SOC_2$. One skilled in the art would recognize and understand how to execute this chemistry in order to produce 4-(2-chloroacetamido)-3-methylbenzoyl chloride. Alternatively, 4-(2-chloroacetamido)-3-methylbenzoic acid was converted to the 4-(2-chloroacetamido)-3-methylbenzoyl chloride using $COCl)_2$. One skilled in the art would recognize and understand how to execute this chemistry in order to produce 4-(2-chloroacetamido)-3-methylbenzoyl chloride. 4-(2-chloroacetamido)-3-methylbenzoyl chloride was coupled to 4-[(4-methylpiperazin-1-yl)methyl]aniline using in tetrahydrifuran in the presence of N,N-diisopropylethylamineto produce 4-(2-chloroacetamido)-3-methyl-N-{4-[(4-methylpiperazin-1-yl)methyl]phenyl}benzamide. One skilled in the art would recognize and understand how to execute this chemistry in order to produce 4-(2-chloroacetamido)-3-methyl-N-{4-[(4-methylpiperazin-1-yl) methyl]phenyl}benzamide.

Step 2: 4-[2-(8-cyano-2H,3H-[1,4]dioxino[2,3-g]quinolin-7-ylsulfanyl)acetamido]-3-methyl-N-4-[(4-methylpiperazin-1-yl)methyl]phenylbenzamide was prepared from 7-sulfanyl-2H,3H-[1,4]dioxino[2,3-g]quinoline-8-carbonitrile and 4-(2-chloroacetamido)-3-methyl-N-{4-[(4-methyl piperazin-1-yl)methyl]phenyl}benzamide using the method described in synthetic procedure 2. The resulting product was converted to the HCl salt using HCl in ether. LCMS MS: 623 (M+H)+.

Example 11: Synthesis of 2-[(8-cyano-2,3-dihydro-[1,4]dioxino[2,3-g]quinolin-7-yl)sulfanyl]-N-[2-methyl-5-(pyrrolidin-1-ylmethyl)phenyl]acetamide-hydrochloride (AP-R235)

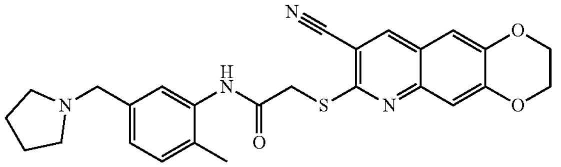 [SMILES: Cc1ccc(CN2CCCC2)cc1NC(=O)CSc1nc2cc3c(cc2cc1C#N)OCCO3]

Step 1: Synthesis of 2-chloro-N-[2-methyl-5-(pyrrolidin-1-ylmethyl)phenyl]acetamide: 4-Methyl-3-nitrobenzaldehyde was converted into 1-[(4-methyl-3-nitro-phenyl)methyl]pyrrolidine by reductive amination using pyrrolidine, sodium triacetoxyborohydride, and catalytic acetic acid in tetrahydrofuran. One skilled in the art would recognize and understand how to execute this chemistry in order to produce 1-[(4-methyl-3-nitro-phenyl)methyl]pyrrolidine. The nitro group of 1-[(4-methyl-3-nitro-phenyl)methyl]pyrrolidine was reduced to the corresponding aniline, 2-methyl-5-(pyrrolidin-1-ylmethyl)aniline, using an excess of tin (II) chloride in ethyl acetate. One skilled in the art would recognize and understand how to execute this chemistry in order to produce 2-methyl-5-(pyrrolidin-1-ylmethyl)aniline. The 2-chloro-N-phenylacetamide intermediate, 2-chloro-N-[2-methyl-5-(pyrrolidin-1-ylmethyl)phenyl]acetamide, was prepared from 2-methyl-5-(pyrrolidin-1-ylmethyl)aniline using the standard procedure 1.

Step 2: 2-[(8-cyano-2,3-dihydro-[1,4]dioxino[2,3-g]quinolin-7-yl)sulfanyl]-N-[2-methyl-5-(pyrrolidin-1-ylmethyl)phenyl]acetamide hydrochloride was prepared from 7-sulfanyl-2H,3H-[1,4]dioxino[2,3-g]quinoline-8-carbonitrile and 2-chloro-N-[2-methyl-5-(pyrrolidin-1-ylmethyl) phenyl]acetamide using the method described in synthetic procedure 2. The resulting product was converted to the HCl salt using HCl in ether. LCMS MS: 475.49 $(M+H)^+$ Example 12: Synthesis of 2-((8-cyano-2,3-dihydro-[1,4]dioxino[2,3-g]quinolin-7-yl)thio)-N-(2-methyl-4-(pyrrolidin-1-ylmethyl)phenyl)acetamide dihydrochloride (AP-R352)

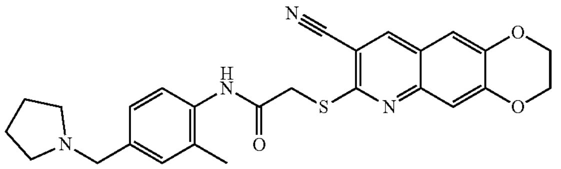 [SMILES: Cc1cc(CN2CCCC2)ccc1NC(=O)CSc1nc2cc3c(cc2cc1C#N)OCCO3]

Step 1: Synthesis of 2-chloro-N-(2-methyl-4-(pyrrolidin-1-ylmethyl)phenyl)acetamide: 3-methyl-4-nitrobenzaldehyde was converted into 1-(3-methyl-4-nitrobenzyl)pyrrolidine by reductive amination using pyrrolidine, sodium triacetoxyborohydride, and catalytic acetic acid in tetrahydrofuran. One skilled in the art would recognize and understand how to execute this chemistry in order to produce 1-(3-methyl-4-nitrobenzyl)pyrrolidine. The nitro group of 1-(3-methyl-4-nitrobenzyl)pyrrolidine was reduced to the corresponding aniline, 2-methyl-4-(pyrrolidin-1-ylmethyl) aniline, using an excess of tin (II) chloride in ethyl acetate. One skilled in the art would recognize and understand how to execute this chemistry in order to produce 2-methyl-4-(pyrrolidin-1-ylmethyl)aniline. The 2-chloro-N-phenylacetamide intermediate, 2-chloro-N-(2-methyl-4-(pyrrolidin-1-ylmethyl)phenyl)acetamide, was prepared from 2-methyl-4-(pyrrolidin-1-ylmethyl)aniline using the standard procedure 1

Step 2: 2-((8-cyano-2,3-dihydro-[1,4]dioxino[2,3-g]quinolin-7-yl)thio)-N-(2-methyl-4-(pyrrolidin-1-ylmethyl)phenyl)acetamide dihydrochloride was prepared from 7-sulfanyl-2H,3H-[1,4]dioxino[2,3-g]quinoline-8-carbonitrile and 2-chloro-N-(2-methyl-4-(pyrrolidin-1-ylmethyl) phenyl)acetamide using the method described in synthetic procedure 2. The resulting product was converted to the HCl salt using HCl in ether. LCMS retention time: 0.5 minutes MS: 475.32 $(M+H)^+$.

Example 13: Synthesis of 2-((8-cyano-2,3-dihydro-[1,4]dioxino[2,3-g]quinolin-7-yl)thio)-N-(1,3-dimethyl-1H-pyrazol-5-yl)acetamide (AP-R357)

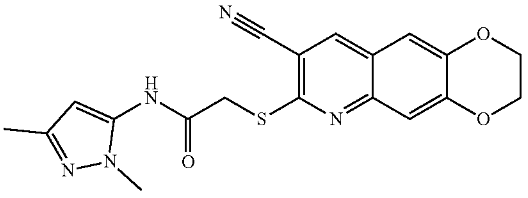 [SMILES: Cc1cc(NC(=O)CSc2nc3cc4c(cc3cc2C#N)OCCO4)n(C)n1]

The title compound was prepared from 7-sulfanyl-2H,3H-[1,4]dioxino[2,3-g]quinoline-8-carbonitrile and 2-chloro-N-(1,3-dimethyl-1H-pyrazol-5-yl)acetamide using the method described in synthetic procedure 2. 2-chloro-N-(1,3-dimethyl-1H-pyrazol-5-yl)acetamide was prepared using the method described in procedure 1 from 1,3-dimethyl-1H-pyrazol-5-amine and chloroacetyl chloride LCMS MS: 396 $(M+H)^+$.

Example 14: Synthesis of 2-((8-cyano-2,3-dihydro-[1,4]dioxino[2,3-g]quinolin-7-yl)thio)-N-(1,3-dimethyl-1H-pyrazol-4-yl)acetamide (AP-R358)

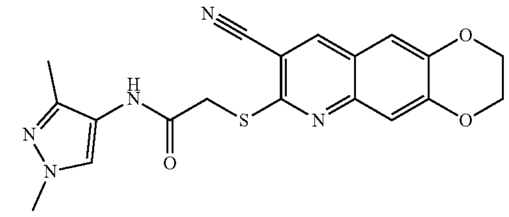

The title compound was prepared from 7-sulfanyl-2H,3H-[1,4]dioxino[2,3-g]quinoline-8-carbonitrile and 2-chloro-N-(1,3-dimethyl-1H-pyrazol-4-yl)acetamide using the method described in synthetic procedure 2. 2-chloro-N-(1,3-dimethyl-1H-pyrazol-4-yl)acetamide was prepared using the method described in procedure 1 from 1,3-dimethyl-1H-pyrazol-4-amine and chloroacetyl chloride. LCMS MS: 396 $(M+H)^+$.

FORMULATIONS

The present invention also relates to compositions or formulations which comprise the kinase inhibitors according to the present invention. In general, the compositions of the present invention comprise an effective amount of one or more of the compounds of the disclosure and salts thereof according to the present invention which are effective for providing treatment or prevention of disease and conditions involving BCR-ABL kinase including cancer; and one or more excipients.

For the purposes of the present invention the term “excipient” and “carrier” are used interchangeably throughout the description of the present invention and said terms are defined herein as, “ingredients which are used in the practice of formulating a safe and effective pharmaceutical composition.”

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), the entire disclosure of which is incorporated by reference herein for all purposes. As used herein, “pharmaceutically acceptable” refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known anticancer agents. Oral formulations containing a compound disclosed herein can comprise any conventionally used oral form, including tablets, capsules, nanoparticles, amorphous solid dispersion, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound (s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids.

Alternatively, the unit dosage form can be a capsule or tablet itself, or it can be the appropriate number of any such compositions in package form. Such unit dosage form can contain from about 1 g/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease.

For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more compounds of the disclosure according to the present invention and one or more excipients; from about 0.01 mg to about 100 mg of one or more compounds of the disclosure according to the present invention and one or more excipients; and from about 0.1 mg to about 10 mg of one or more compounds of the disclosure according to the present invention; and one or more excipients.

PROCEDURES

The following procedures can be utilized in evaluating and selecting compounds as anticancer agents and as kinase inhibitors.

Cytotoxicity assay: CML patient derived cell lines K562 expressing BCR-ABL T315I, Ph+ALL cell line BV173-T315I, and mouse cell line Ba/F3 T315I were used for cytotoxicity testing. All these cell lines express T315I mutant of BCR-ABL. BV-173-T315I is also a model for blast crisis, the terminal stage in CML. Cell lines were cultured in Iscove's Modified Dulbecco's Medium (IMDM) containing L-glutamine and 25 mM Hepes. The cells were maintained at 37° C. in a humidified $CO_2$ incubator. For cytotoxicity measurement 5000-8000 cells were plated into 96 well plates in quadruplicates. Drugs were dissolved in DMSO and cells were treated in increasing doses ranging from 1 to 107 fold. Control cells were treated with respective amounts of DMSO. Cells were incubated for 72 hours and, at the end of the incubation point cell, viability was determined. For this purpose, 25 μl of the cell culture from the 96 well plates were transferred to Ultracruz® black bottom 96 well plates (Santa Cruz Biotechnology) and 25 μl of a live cell detecting fluorescent reagent (Cellular Technology Limited ("CTL")) was added to the cells. The cells and the CTL reagent was mixed thoroughly and centrifuged for 5 min, at the standard g levels normally used to accelerate settling of the cells to the bottom of the culture medium container without damaging the living cells, and the fluorescence was detected at 405 nm excitation using a CTL scanner. Viable cells will fluoresce green and the machine automatically scans and counts the number of viable cells from each well. The percentage of viable cells in drug treated samples relative to the number of viable cells in DMSO treated samples was then calculated. The data obtained were analyzed using Prism nonlinear regression software (Graphpad Software) for the curve fitting and determination of IC50 values.

Figure 2:
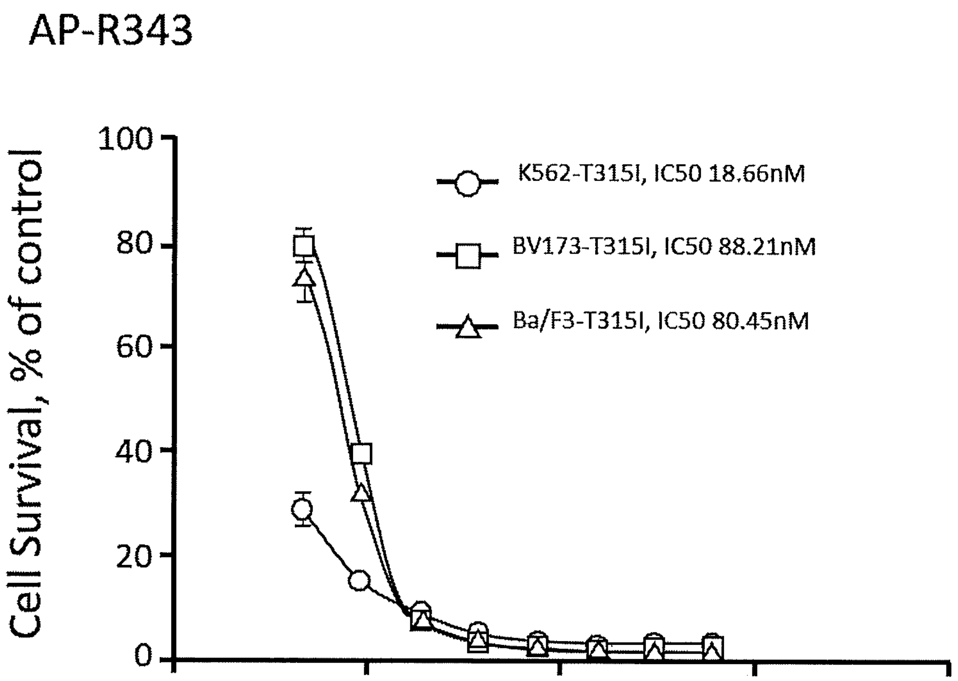
FIG. 2 shows a graph of the relative survival rate of chronic myeloid leukemia cells of cell lines K562-T315I, BV173-T315I, and Ba/F3-T315I relative to the control, which is DMSO without the kinase inhibitor compound, as a function of the dose of the kinase inhibitor compound for kinase inhibitor compound AP-R343.
Figure 3A:
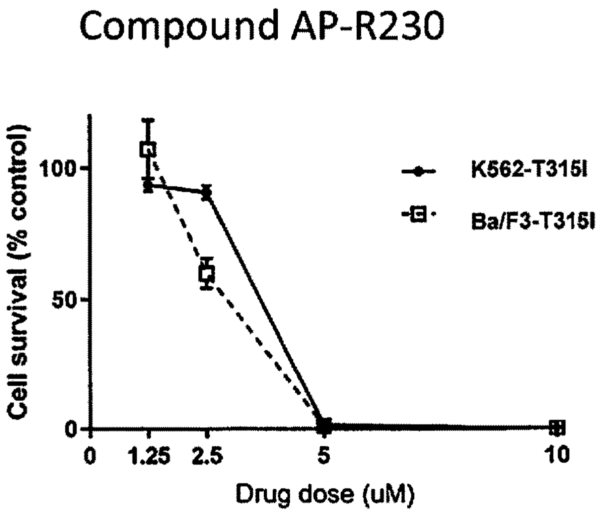
FIG. 3(*a*) shows a graph of the relative survival rate of chronic myeloid leukemia cells of cell lines K562-T315I and Ba/F3-T315I relative to the control, which is DMSO without the kinase inhibitor compound, as a function of the dose of the kinase inhibitor compound for kinase inhibitor compound AP-R230.
Figure 3B:
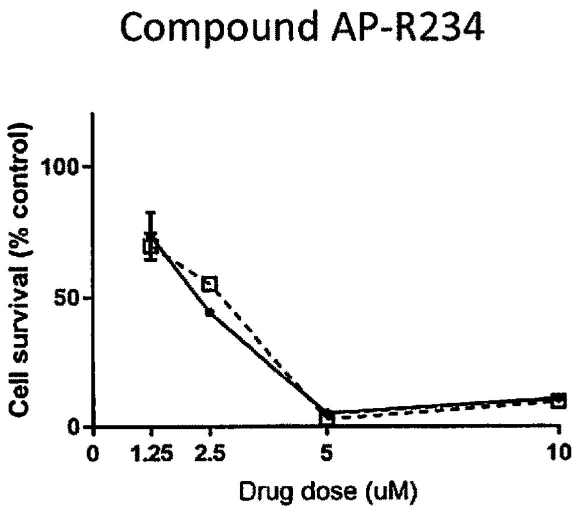
Figure 3C:
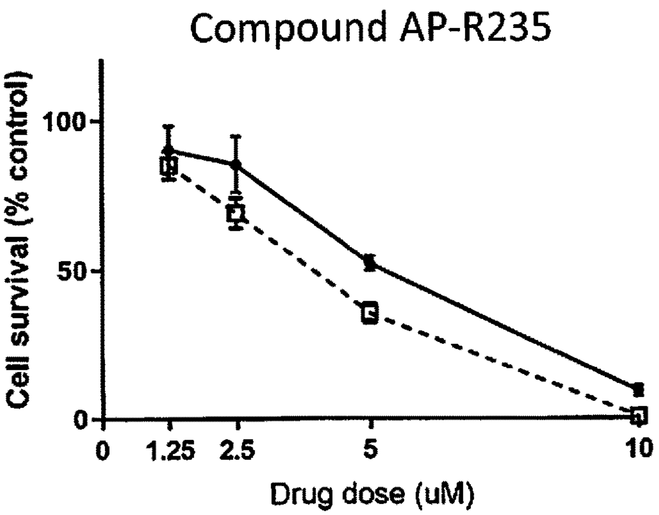
Figure 3D:
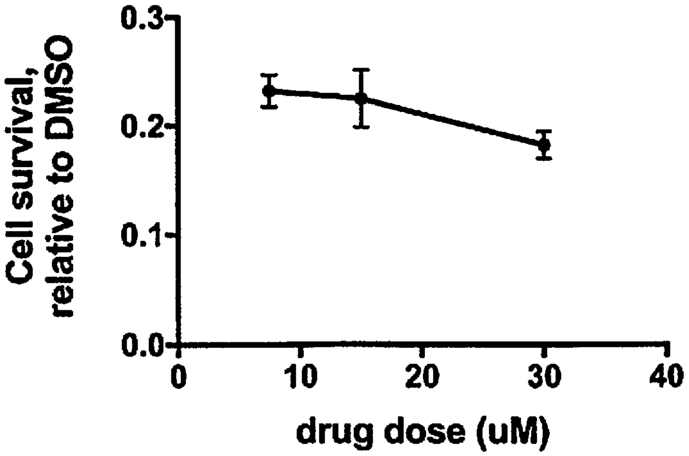
Figure 3E:
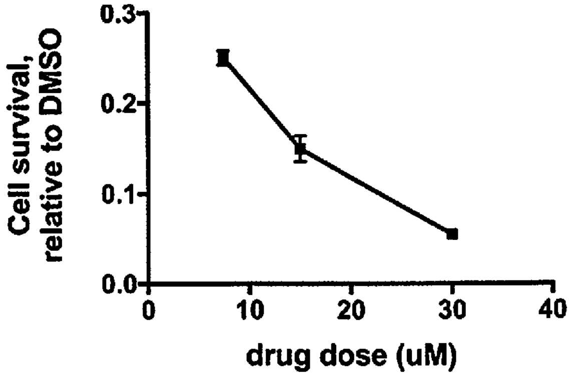
Figure 3F:
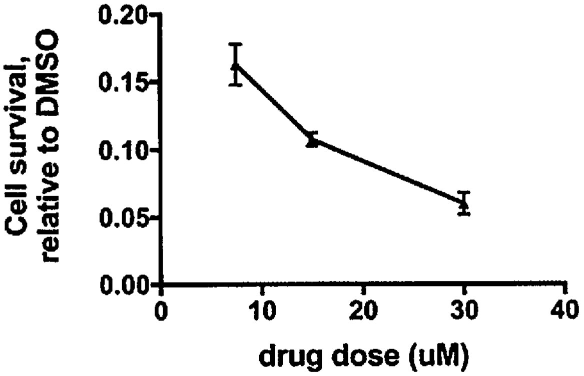

The results are shown graphically in FIGS. 1 through 5. Referring to FIG. 1, treatment with the compound AP-R342 resulted in cancer cell survival rates of less than about 7 percent compared to the DMSO control at dosages (concentrations) of about $10^{-6}$ M to about 10-M for all three of the cancer cell lines tested. Referring to FIG. 2, treatment with the compound AP-R343 resulted in cancer cell survival rates of less than about 5 percent compared to the DMSO control at dosages (concentrations) of about $10^{-6}$ M to about $10^{-5}$ M for all three of the cancer cell lines tested.

Referring to FIG. 3(*a*), treatment with the compound AP-R230 resulted in a cancer cell survival rates of less than about 4 percent to near complete destruction of the cancer cells compared to the DMSO control at dosages (concentrations) of about 5 μM to about 10 μM for cell lines K562-T315I and Ba/F3-T315I.

Referring to FIG. 3(*b*), treatment with the compound AP-R234 resulted in cancer cell survival rates of less than about 4 percent compared to the DMSO control at dosages (concentrations) of about 5 μM for cell lines K562-T315I and Ba/F3-T315I.

Referring to FIG. 3(*c*), treatment with the compound AP-R235 resulted in cancer cell survival rates of less than about 10 percent compared to the DMSO control at dosages (concentrations) of about 10 μM for the cell line K562-T315I and less than about 2 percent compared to the DMSO control at dosages (concentrations) of about 10 μM for the cell line Ba/F3-T315I.

Referring to FIG. 3(*d*), treatment with the compound AP-R357 resulted in cancer cell survival rates of less than about 20 percent compared to the DMSO control at dosages (concentrations) of about 30 μM for the cell line K562-T315I.

Referring to FIG. 3(*e*), treatment with the compound AP-R357 resulted in cancer cell survival rates of less than about 6 percent compared to the DMSO control at dosages (concentrations) of about 30 μM for the cell line BV173-T315I.

Referring to FIG. 3(*f*), treatment with the compound AP-R357 resulted in cancer cell survival rates of less than about 7 percent compared to the DMSO control at dosages (concentrations) of about 30 μM for the cell line Ba/F3-T315I.

Figure 4:
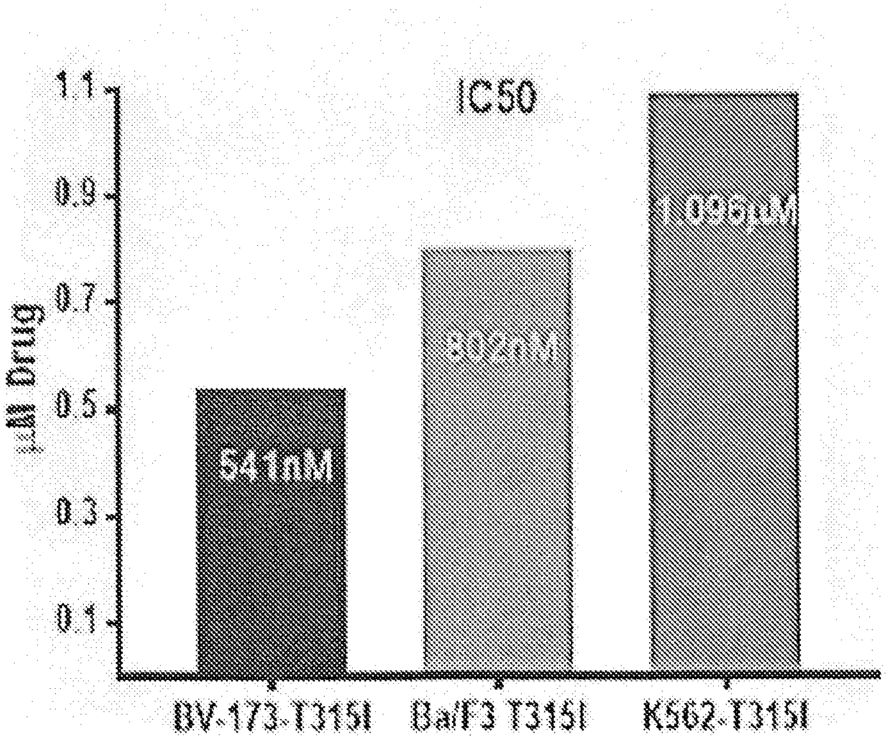
FIG. 4 shows the bar diagram of $IC_{50}$ values of chronic myeloid leukemia cell lines BV173-T315I, Ba/F3-T315I and K562-T315I treated with the kinase inhibitor compound AP-R352. IC50 values were calculated from the survival rate normalized to the control which is DMSO without the kinase inhibitor as a function of the dose of the kinase inhibitor compound AP-R352.

Referring to FIG. 4, treatment with the compound AP-R352 showed that the IC50s for cell killing were 0.541 μM, 0.80 μM and 1.09 μM for cell lines BV173-T315I, Ba/F3-T315I and K562-T315I respectively.

Figure 5:
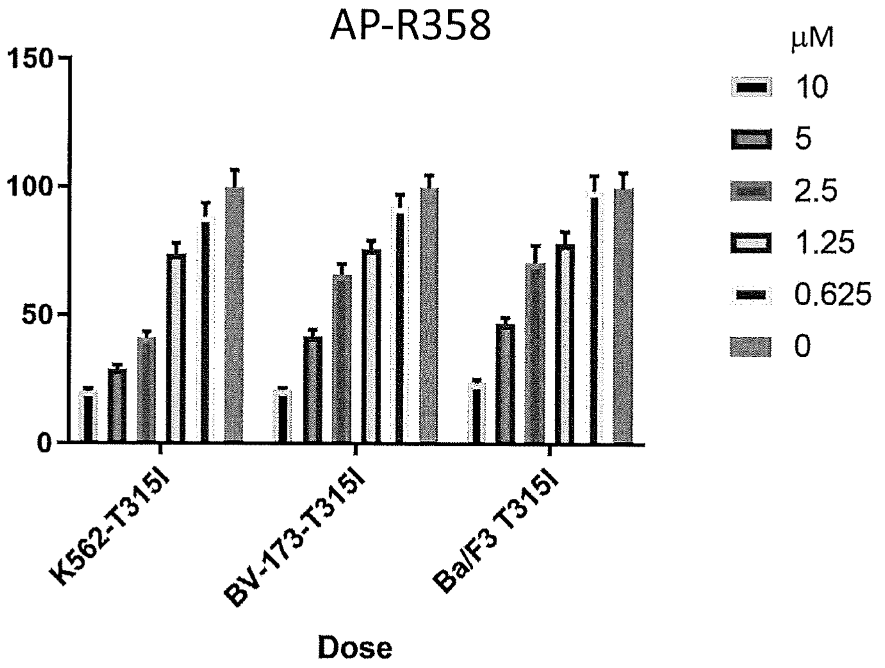
FIG. 5 shows the bar diagram of survival of chronic myeloid leukemia cell lines BV173-T315I, Ba/F3-T315I and K562-T315I treated with varying concentrations of the kinase inhibitor compound AP-R358 and the control DMSO without the kinase inhibitor compound.

Referring to FIG. 5, treatment with the compound AP-R358 resulted in about 20% cell survival (80% cell death) at 10 mM and above 90% survival (10% cell death) at 0.625 mM in cell lines K562-T315I, BV173-T315I and Ba/F3-T315.

What is claimed is:

1. A compound having formula (I):

(I)

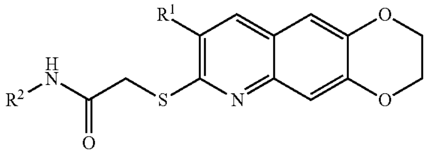

or an enantiomer, diastereomer, tautomer or pharmaceutically acceptable salt thereof, wherein:

$R^1$ is selected from the group consisting of $C_{1-6}$ alkyl and nitrile;

$R^2$ is selected from the group consisting of

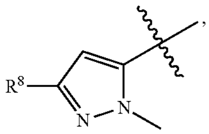,

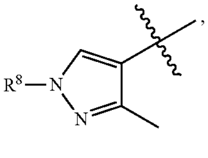,

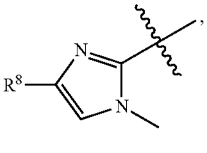,

-continued

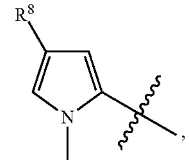 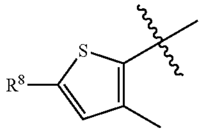

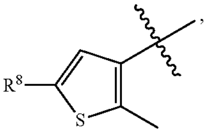 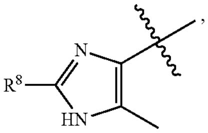

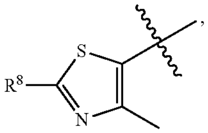 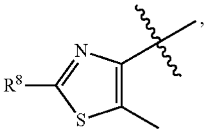 and

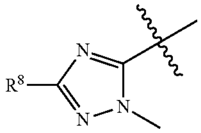

and $R^8$ is selected from the group consisting of hydrogen, $C_{1-6}$ alkyl, $C_{1-6}$ haloalkyl, $C_{3-7}$ branched alkyl, and $C_{3-7}$ cycloalkyl.

2. The compound of claim 1 having the formula (III)

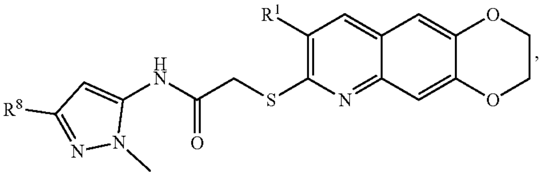

(IV)

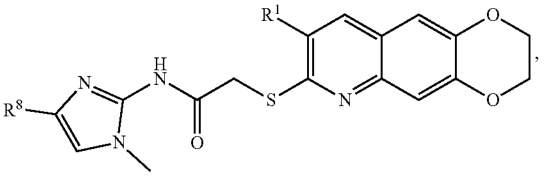

(V)

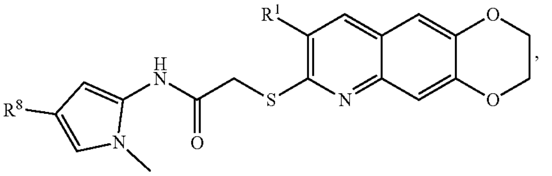

(VI)

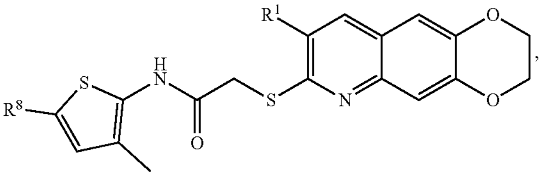

-continued (VII)

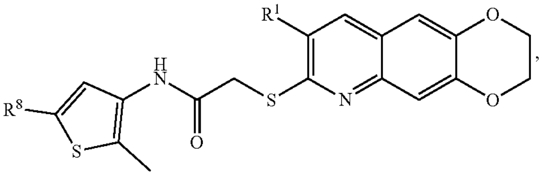

(VIII)

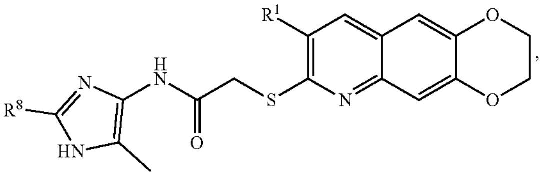

(IX)

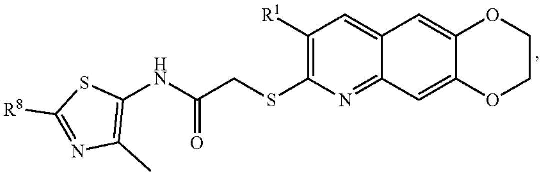

(X)

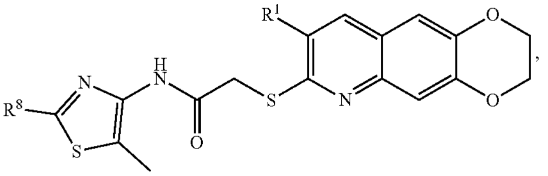

(XI)

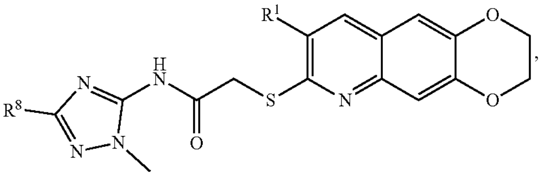 or (XII)

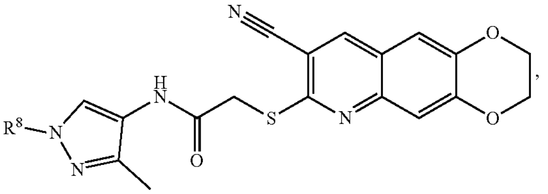

or an enantiomer, diastereomer, tautomer or pharmaceutically acceptable salt thereof.

3. The compound according to claim 1 selected from the group consisting of 2-((8-cyano-2,3-dihydro-[1,4]dioxino[2,3-g]quinolin-7-yl)thio)-N-(1,3-dimethyl-1H-pyrazol-5-yl)acetamide;

2-((8-cyano-2,3-dihydro-[1,4]dioxino[2,3-g]quinolin-7-yl)thio)-N-(1,3-dimethyl-1H-pyrazol-4-yl)acetamide; and pharmaceutically acceptable salts thereof.

4. A pharmaceutical composition comprising an effective amount of at least one compound according to claim 1 and at least one pharmaceutically acceptable excipient.

5. The pharmaceutical composition according to claim 4, wherein the at least one compound is at least one member selected from the group consisting of:

24(8-cyano-2,3-dihydro-[1,4]dioxino[2,3-g]quinolin-7-yl)thio)-N-(1,3-dimethyl-1H-pyrazol-5-yl)acetamide;

2-((8-cyano-2,3-dihydro-[1,4]dioxino[2,3-g]quinolin-7-yl)thio)-N-(1,3-dimethyl-1H-pyrazol-4-yl)acetamide; and pharmaceutically acceptable salts thereof.

6. A method for treating chronic myeloid leukemia in a subject in need thereof, said method comprising administering to the subject an effective amount of at least one compound according to claim 1.

7. The method of claim 6, wherein the at least one compound is administered in a composition further comprising at least one pharmaceutically acceptable excipient.

* * * * *